(12) United States Patent
Miyazaki

(10) Patent No.: US 11,515,486 B2
(45) Date of Patent: Nov. 29, 2022

(54) ORGANIC ELECTROLUMINESCENCE DEVICE AND POLYCYCLIC COMPOUND FOR ORGANIC ELECTROLUMINESCENCE DEVICE

(71) Applicant: SAMSUNG DISPLAY CO., LTD., Yongin-si (KR)

(72) Inventor: Yuuki Miyazaki, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 707 days.

(21) Appl. No.: 16/427,620

(22) Filed: May 31, 2019

(65) Prior Publication Data
US 2020/0013962 A1 Jan. 9, 2020

(30) Foreign Application Priority Data
Jul. 3, 2018 (KR) .......................... 10-2018-0076993

(51) Int. Cl.
*H01L 51/00* (2006.01)
*C07F 7/08* (2006.01)
(Continued)

(52) U.S. Cl.
CPC ........ *H01L 51/0072* (2013.01); *C07D 405/04* (2013.01); *C07D 409/04* (2013.01);
(Continued)

(58) Field of Classification Search
CPC .. C07D 405/04; C07D 409/04; C07D 413/04; C07F 7/0816; H01L 51/0061;
(Continued)

(56) References Cited

U.S. PATENT DOCUMENTS 8,367,224 B2 * 2/2013 Katakura ............... C09K 11/06
313/506
9,324,949 B2 4/2016 Kwong et al.
(Continued)

FOREIGN PATENT DOCUMENTS

EP 3 072 943 A1 9/2016
KR 10-2015-0009461 A 1/2015
(Continued)

OTHER PUBLICATIONS

Gan et al., J. Phys. Chem. Lett., (2018), vol. 9, pp. 4725-4731. (Year: 2018).*
(Continued)

*Primary Examiner* — Dawn L Garrett
(74) *Attorney, Agent, or Firm* — Lewis Roca Rothgerber Christie LLP

(57) ABSTRACT

An organic electroluminescence device includes a first electrode, a hole transport region on the first electrode, an emission layer on the hole transport region, the emission layer including a polycyclic compound, an electron transport region on the emission layer, and a second electrode on the electron transport region, wherein the polycyclic compound includes an isophthalonitrile derivative, a linker, and a nitrogen-containing group, the linker is a condensed cyclic group of three rings that are independently five-membered or six-membered rings, and each of the isophthalonitrile derivative and the nitrogen-containing group is substituted into a same ring of the linker.

20 Claims, 2 Drawing Sheets

(51) Int. Cl.
    *C07D 409/04*     (2006.01)
    *C07D 405/04*     (2006.01)
    *C07D 413/04*     (2006.01)
    *H01L 51/50*     (2006.01)

(52) U.S. Cl.
    CPC .......... *C07D 413/04* (2013.01); *C07F 7/0816* (2013.01); *H01L 51/0061* (2013.01); *H01L 51/0073* (2013.01); *H01L 51/0074* (2013.01); *H01L 51/0094* (2013.01); *H01L 51/5012* (2013.01)

(58) Field of Classification Search
    CPC ............. H01L 51/0072; H01L 51/0073; H01L 51/0074; H01L 51/0094; H01L 51/5012

See application file for complete search history.

(56) References Cited

U.S. PATENT DOCUMENTS

| | | | |
|---|---|---|---|
| 9,780,312 | B2 | 10/2017 | Lee et al. |
| 2018/0166634 | A1* | 6/2018 | Numata .............. H01L 51/0067 |

FOREIGN PATENT DOCUMENTS

| | | |
|---|---|---|
| KR | 10-2016-0045507 A | 4/2016 |
| KR | 10-2017-0035376 A | 3/2017 |
| KR | 10-2017-0037135 A | 4/2017 |
| WO | WO 2016/116520 A1 | 7/2016 |
| WO | WO 2016/129672 A1 | 8/2016 |

OTHER PUBLICATIONS

Yirang IM et al. Molecular Design Strategy of Organic Thermally Activated Delayed Fluorescence Emitters, Chemistry of Materials, Feb. 7, 2017.

* cited by examiner

ORGANIC ELECTROLUMINESCENCE DEVICE AND POLYCYCLIC COMPOUND FOR ORGANIC ELECTROLUMINESCENCE DEVICE

CROSS-REFERENCE TO RELATED APPLICATION

Korean Patent Application No. 10-2018-0076993, filed on Jul. 3, 2018, in the Korean Intellectual Property Office, and entitled: "Organic Electroluminescence Device and Polycyclic Compound for Organic Electroluminescence Device," is incorporated by reference herein in its entirety.

BACKGROUND

1. Field

Embodiments relate to an organic electroluminescence device and a polycyclic compound for the organic electroluminescence device.

2. Description of the Related Art

Recently, the development of an organic electroluminescence display device as an image display device is being actively conducted. Different from a liquid crystal display device, the organic electroluminescence display device is so-called a self-luminescent display device in which holes and electrons injected from a first electrode and a second electrode recombine in an emission layer, and a light emission material including an organic compound in the emission layer emits light to attain display.

In the application of an organic electroluminescence device to a display device, the decrease of the driving voltage, and the increase of the light-emitting efficiency and the life of the organic electroluminescence device are required, and developments on materials for an organic electroluminescence device stably attaining the requirements are being continuously required.

SUMMARY

Embodiments are directed to an organic electroluminescence device, including a first electrode, a hole transport region on the first electrode, an emission layer on the hole transport region, the emission layer including a polycyclic compound, an electron transport region on the emission layer, and a second electrode on the electron transport region, wherein the polycyclic compound includes an isophthalonitrile derivative, a linker, and a nitrogen-containing group, the linker is a condensed cyclic group of three rings that are independently five-membered or six-membered rings, and each of the isophthalonitrile derivative and the nitrogen-containing group is substituted into a same ring of the linker.

In an embodiment, the emission layer may emit delayed fluorescence. The emission layer may be a delayed fluorescence emission layer including a host and a dopant, and the host may be the polycyclic compound.

In an embodiment, the emission layer may be a thermally activated delayed fluorescence emission layer that emits blue light.

In an embodiment, the polycyclic compound may have an absolute value of a difference between a singlet energy level and a triplet energy level of about 0.1 eV or less.

In an embodiment, the polycyclic compound may be represented by the following Formula 1:

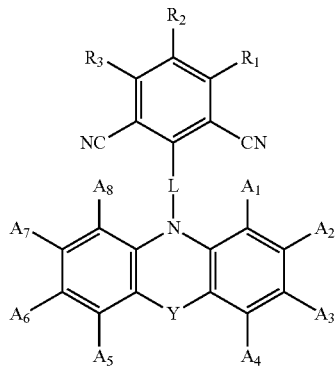

[Formula 1]

In Formula 1, Y may be $CR_{11}R_{11}$, $SiR_{12}R_{13}$, O, S, or a direct linkage, $R_1$ to $R_3$ may each independently be a hydrogen atom, a deuterium atom, a halogen atom, a cyano group, $SiR_{14}R_{15}$, $SR_{16}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $A_1$ to $A_8$ and $R_{10}$ to $R_{16}$ may each independently be a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and L may be represented by following Formula 2:

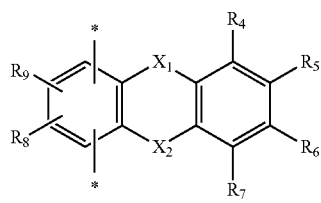

[Formula 2]

In Formula 2, $X_1$ and $X_2$ may each independently be a direct linkage, $CR_{17}R_{18}$, $SiR_{19}R_{20}$, O, or S, $R_4$ to $R_9$ may each independently be a hydrogen atom, a deuterium atom, a halogen atom, a cyano group, $SiR_{21}R_{22}$, $OR_{23}$, $SR_{24}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and $R_{17}$ to $R_{24}$ may each independently be a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In an embodiment, $R_1$ and $R_3$ of Formula 1 may each independently be a hydrogen atom, and $R_2$ may be a hydrogen atom, a cyano group, $SiR_{14}R_{15}$, $SR_{16}$, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In an embodiment, Formula 1 may be represented by following Formula 3:

[Formula 3]

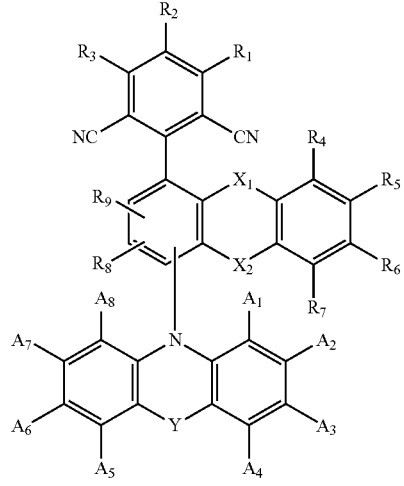

In Formula 3, Y, $A_1$ to $A_8$, $X_1$, $X_2$, and $R_1$ to $R_9$ are the same as defined in Formula 1 and Formula 2.

In an embodiment, Formula 3 may be represented by any one among the following Formula 3-1 to Formula 3-3:

[Formula 3-2]

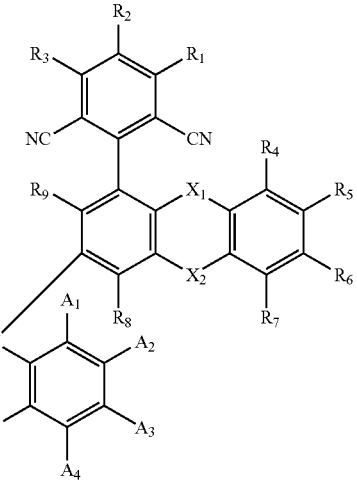

[Formula 3-3]

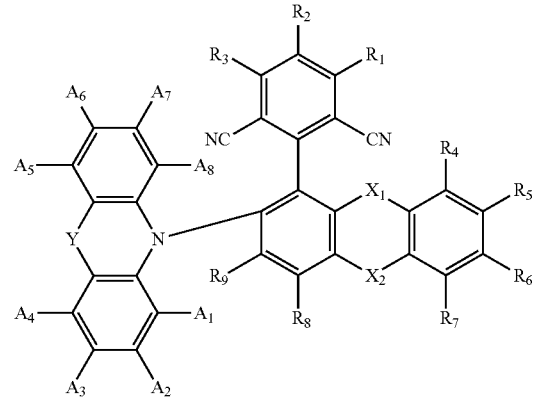

In Formula 3-1 to Formula 3-3, Y, $A_1$ to $A_8$, $X_1$, $X_2$, and $R_1$ to $R_9$ are the same as defined in Formula 1 and Formula 2.

In an embodiment, Formula 3 may be represented by any one among the following Formula 4-1 to Formula 4-3:

[Formula 3-1]

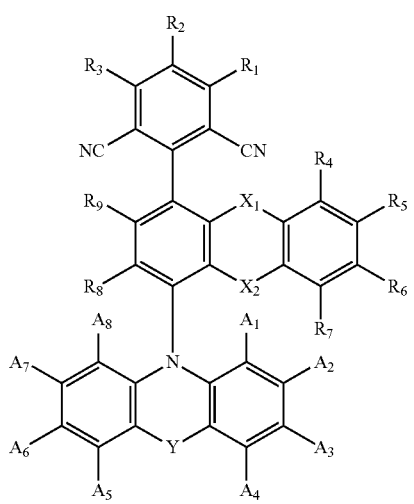

[Formula 4-1]

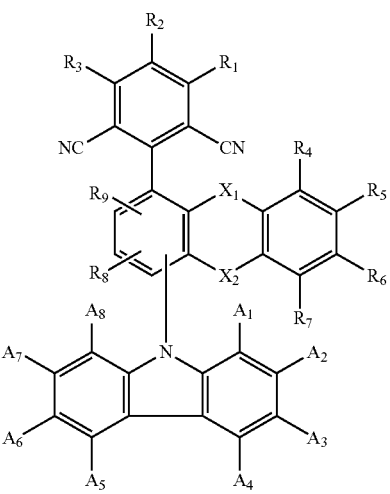

Embodiments are also directed to a polycyclic compound represented by the following Formula 1:

[Formula 1]

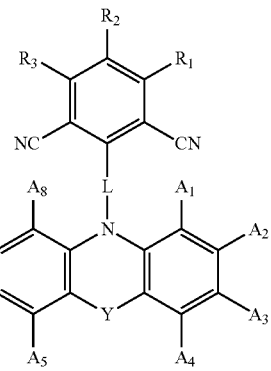

In Formula 1, Y may be $CR_{10}R_{11}$, $SiR_{12}R_{13}$, O, S, or a direct linkage, $R_1$ to $R_3$ may each independently be a hydrogen atom, a deuterium atom, a halogen atom, a cyano group, $SiR_{14}R_{15}$, $SR_{16}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $A_1$ to $A_8$ and $R_{10}$ to $R_{16}$ may each independently be a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and L may be represented by following Formula 2:

[Formula 2]

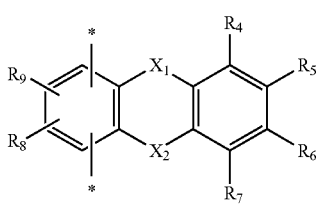

In Formula 2, $X_1$ and $X_2$ may each independently be a direct linkage, $CR_{17}R_{18}$, $SiR_{19}R_{20}$, O, or S, $R_4$ to $R_9$ may each independently be a hydrogen atom, a deuterium atom, a halogen atom, a cyano group, $SiR_{21}R_{22}$, $OR_{23}$, $SR_{24}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and $R_{17}$ to $R_{24}$ may each independently be a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

BRIEF DESCRIPTION OF THE DRAWINGS

Features will become apparent to those of skill in the art by describing in detail example embodiments with reference to the attached drawings in which:

-continued

[Formula 4-2]

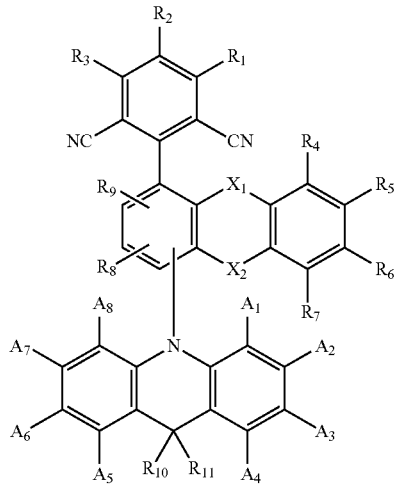

[Formula 4-3]

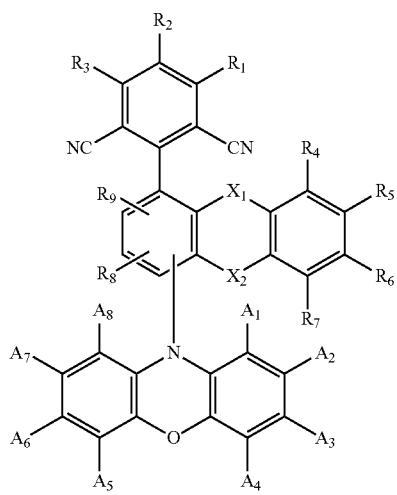

In Formula 4-1 to Formula 4-3, $A_1$ to $A_8$, $X_1$, $X_2$, and $R_1$ to $R_{11}$ are the same as defined in Formula 1 and Formula 2.

Embodiments are also directed to an organic electroluminescence device, including a first electrode, a hole transport region on the first electrode, an emission layer on the hole transport region, an electron transport region on the emission layer, and a second electrode on the electron transport region, wherein the emission layer includes the polycyclic compound represented by Formula 1.

Figure 1:
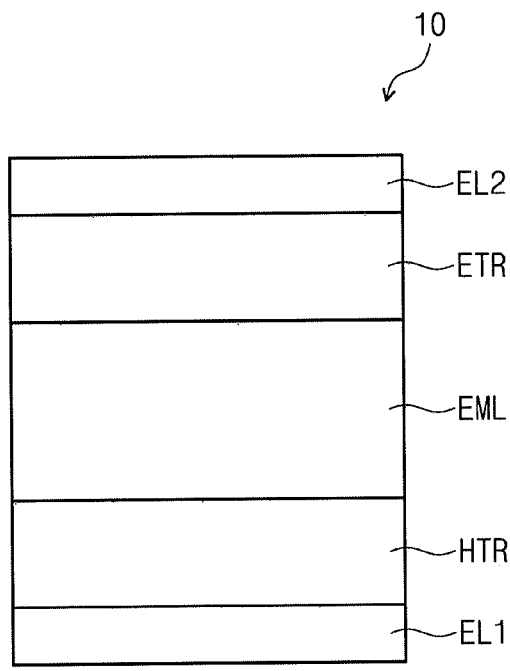
Figure 2:
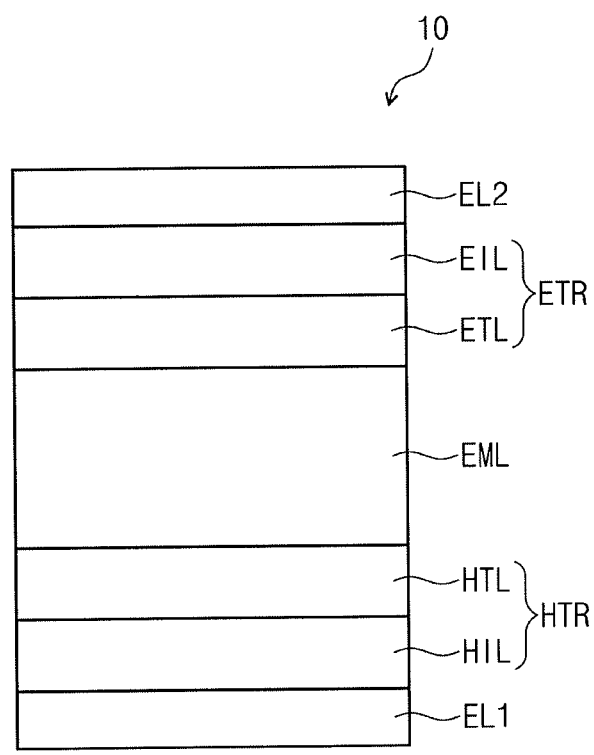
Figure 3:
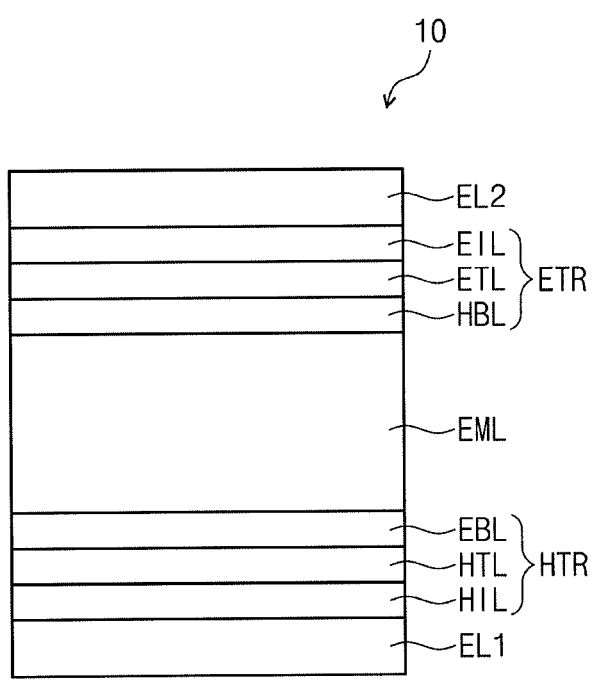

FIG. 1 is a cross-sectional view schematically illustrating an organic electroluminescence device according to an example embodiment;

FIG. 2 is a cross-sectional view schematically illustrating an organic electroluminescence device according to an example embodiment; and FIG. 3 is a cross-sectional view schematically illustrating an organic electroluminescence device according to an example embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

It will be understood that, although the terms first, second, etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof. It will also be understood that when a layer, a film, a region, a plate, etc. is referred to as being "on" another part, it can be "directly on" the other part, or intervening layers may also be present.

Hereinafter, an organic electroluminescence device according to example embodiments will be explained with reference to FIGS. 1 to 3.

Referring to FIGS. 1 to 3, an organic electroluminescence device 10 according to an example embodiment may include a first electrode EL1, a hole transport region HTR, an emission layer EML, an electron transport region ETR, and a second electrode EL2, laminated one by one.

The first electrode EL1 and the second electrode EL2 may be oppositely disposed from each other, and a plurality of organic layers may be disposed between the first electrode EL1 and the second electrode EL2. The plurality of the organic layers may include a hole transport region HTR, an emission layer EML, and an electron transport region ETR. The organic electroluminescence device 10 of an example embodiment may include the polycyclic compound of an example embodiment in the emission layer EML.

Compared to FIG. 1, FIG. 2 shows the cross-sectional view of an organic electroluminescence device 10 of an example embodiment, wherein a hole transport region HTR includes a hole injection layer HIL and a hole transport layer HTL, and an electron transport region ETR includes an electron injection layer EIL and an electron transport layer ETL. Compared to FIG. 1, FIG. 3 shows the cross-sectional view of an organic electroluminescence device 10 of an example embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL.

In the organic electroluminescence devices 10 of example embodiments shown in FIGS. 1 to 3, the polycyclic compound of an example embodiment may be included in at least one organic layer among the plurality of organic layers.

The first electrode EL1 may have conductivity, and may be formed using a metal alloy or a conductive compound. The first electrode EL1 may be an anode.

The first electrode EL1 may be a transmissive electrode, a transflective electrode, or a reflective electrode. When the first electrode EL1 is the transmissive electrode, the first electrode EL1 may be formed using a transparent metal oxide such as indium tin oxide (ITO), indium zinc oxide (IZO), zinc oxide (ZnO), and indium tin zinc oxide (ITZO). When the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The first electrode EL1 may have a structure including a plurality of layers including a reflective layer or a transflective layer formed using the above materials, and a transmissive conductive layer formed using ITO, IZO, ZnO, or ITZO. For example, the first electrode EL1, may include a plurality of layers of ITO/Ag/ITO.

The hole transport region HTR may be provided on the first electrode EL1. The hole transport region HTR may include at least one of a hole injection layer HIL, a hole transport layer HTL, a hole buffer layer, or an electron blocking layer EBL.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL, or a hole transport layer HTL, and may have a structure of a single layer formed using a hole injection material and a hole transport material. In an implementation, the hole transport region HTR may have a structure of a single layer formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/ electron blocking layer EBL.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL of the organic electroluminescence device 10 may include a suitable hole injection material. For example, the hole injection layer HIL may include triphenylamine-containing polyetherketone (TPA-PEK), 4-isopropyl-4'-methyldiphenyliodoniumtetrakis(pentafluorophenyl)borate (PPBI), N,N'-diphenyl-N,N'-bis-[4-(phenyl-m-tolyl-amino)-phenyl]-phenyl-4,4'-diamine (DNTPD), a phthalocyanine compound such as copper phthalocyanine, 4,4',4"-tris(3-methyl phenyl phenylamino)

triphenylamine (m-MTDATA), N,N'-di(1-naphthyl)-N,N'-diphenylbenzidine (NPB), N,N'-bis(1-naphthyl)-N,N'-diphenyl-4,4'-diamine (α-NPD), 4,4',4"-tris(N,N-diphenylamino)triphenylamine (TDATA), 4,4',4"-tris(N,N-2-naphthyl phenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or dipyrazino[2,3-f:2',3'-h]quinoxaline-2,3,6,7,10,11-hexacarbonitrile (HAT-CN).

The hole transport layer HTL of the organic electroluminescence device 10 may include a suitable hole transport material. For example, the hole transport layer HTL may include 1,1-bis[(di-4-trileamino)phenyl]cyclohexane (TAPC), carbazole derivatives such as N-phenyl carbazole and polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), N,N'-bis(1-naphthyl)-N,N'-diphenyl 4,4'-diamine (α-NPD), etc.

The hole transport region HTR may further include an electron blocking layer EBL, and the electron blocking layer EBL may be disposed between a hole transport layer HTL and an emission layer EML. The electron blocking layer EBL may play the role of preventing electron injection from an electron transport region ETR to a hole transport region HTR.

The electron blocking layer EBL may include a suitable material. The electron blocking layer EBL may include, for example, carbazole derivatives such as N-phenylcarbazole, and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl)triphenylamine (TCTA), N,N'-di(naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), mCP, etc. In addition, as described above, the electron blocking layer EBL may include the polycyclic compound according to an example embodiment.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may include a charge generating material in addition to the above-described materials to improve conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds. For example, non-limiting examples of the p-dopant may include quinone derivatives such as tetracyanoquinodimethane (TCNQ) and 2,3,5,6-tetrafluoro-tetracyanoquinodimethane (F4-TCNQ), metal oxides such as tungsten oxide and molybdenum oxide.

As described above, the hole transport region HTR may include at least one of a hole buffer layer or an electron blocking layer EBL in addition to the hole injection layer HIL and the hole transport layer HTL. The hole buffer layer may compensate a resonance distance according to the wavelength of light emitted from the emission layer EML and increase light emission efficiency. Materials included in the hole transport region HTR may be used as materials included in the hole buffer layer.

The emission layer EML may be provided on the hole transport region HTR. The emission layer EML may have a thickness of, for example, about 100 Å to about 600 Å. The emission layer EML may have a single layer formed using a single material, a single layer formed using a plurality of different materials, or a multilayer structure having a plurality of layers formed using a plurality of different materials.

The emission layer EML may emit one of red light, green light, blue light, white light, yellow light, and cyan light. The emission layer EML may include a fluorescence emitting material or a phosphorescence emitting material.

In an example embodiment, the emission layer EML may be a fluorescence emission layer. For example, a portion of the light emitted from the emission layer EML may be attributed to thermally activated delayed fluorescence (TADF). For example, the emission layer EML may include a light-emitting component that emits thermally activated delayed fluorescence. In an example embodiment, the emission layer EML may be an emission layer emitting thermally activated delayed fluorescence that emits blue light. The light-emitting component emitting thermally activated delayed fluorescence may include a material having excellent charge separation degree (q amount) in a molecule.

In an example embodiment, the emission layer EML includes a polycyclic compound that includes an isophthalonitrile derivative, a linker, and a nitrogen-containing group. The polycyclic compound may be a condensed cyclic compound that includes three or more condensed five-membered (e.g., pentagonal) or six-membered (e.g., hexagonal) rings, for example, a condensed cyclic compound that includes one or more five-membered rings and two or more six-membered rings condensed together. The isophthalonitrile derivative and the nitrogen-containing group of the polycyclic compound may be substituted into the same ring, i.e., a same five-membered ring or a same six-membered ring, of the linker.

In an example embodiment, the emission layer EML may include a host and a dopant, and the host may include a polycyclic compound that includes an isophthalonitrile derivative, a linker, and a nitrogen-containing group.

Herein, —* means a connecting position.

Herein, the term "substituted or unsubstituted" corresponds to substituted or unsubstituted with at least one substituent selected from the group of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocyclic group. In addition, each of the substituents may be substituted or unsubstituted. For example, a biphenyl group may be interpreted as an aryl group or a phenyl group substituted with a phenyl group.

Herein, the halogen atom may be a fluorine atom, a chlorine atom, a bromine atom or an iodine atom.

Herein, the alkyl may be a linear, branched or cyclic type. The carbon number of the alkyl may be 1 to 50, 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

Herein, the aryl group means an optional functional group or substituent derived from an aromatic hydrocarbon ring. The aryl group may be a monocyclic aryl group or a polycyclic aryl group. The carbon number for forming a ring in the aryl group may be, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc.

Herein, the heteroaryl may be a heteroaryl including at least one of O, N, P, Si or S as a heteroatom. The carbon number for forming a ring of the heteroaryl may be 2 to 30, or 2 to 20. The heteroaryl may be monocyclic heteroaryl or polycyclic heteroaryl. Examples of the polycyclic heteroaryl may have a dicyclic or tricyclic structure. Examples of the heteroaryl may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzosilole, dibenzofuran, etc.

Herein, the silyl group includes an alkyl silyl group and an aryl silyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc.

Herein, the carbon number of the amine group may be 1 to 30. The amine group may include an alkyl amine group and an aryl amine group. Examples of the amine group include a methylamine group, a dimethylamine group, a phenylamine group, a naphthylamine group, a 9-methylanthracenylamine group, a triphenylamine group, etc.

Referring to FIGS. 1 to 3 again, the emission layer EML may include a polycyclic compound represented by the following Formula 1:

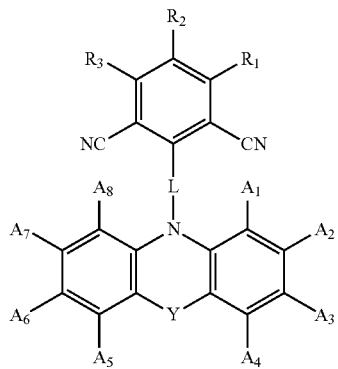

[Formula 1]

In Formula 1, Y may be $CR_{10}R_{11}$, $SiR_{12}R_{13}$, O, S, or a direct linkage.

In Formula 1, $R_1$ to $R_3$ may each independently be a hydrogen atom, a deuterium atom, a halogen atom, a cyano group, $SiR_{14}R_{15}$, $SR_{16}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In Formula 1, $A_1$ to $A_8$ and $R_{10}$ to $R_{16}$ may each independently be a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In the polycyclic compound of an example embodiment, represented by Formula 1:

a

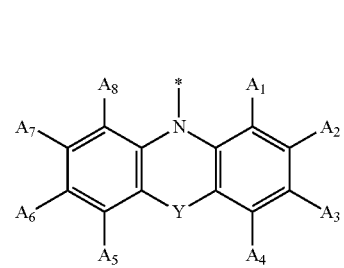

part which is a nitrogen-containing group may be an electron donor moiety, and a

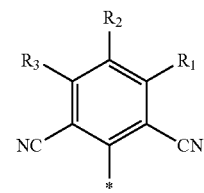

part which is an isophthalonitrile derivative may be an electron acceptor moiety.

The isophthalonitrile derivative is connected with a linker L via a ring carbon that is at an ortho position with respect to carbon into which a cyano group is substituted, and the nitrogen-containing group is connected with the linker L via N.

The linker L, which connects the nitrogen-containing group with the isophthalonitrile derivative, may be represented by the following Formula 2:

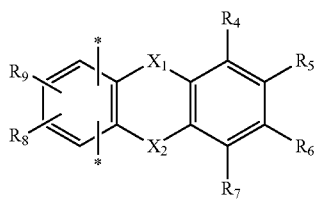

[Formula 2]

In Formula 2, $X_1$ and $X_2$ may each independently be a direct linkage, $CR_{17}R_{18}$, $SiR_{19}R_{20}$, O, or S. In an implementation, $X_1$ and $X_2$ are not both direct linkages at the same time. When $X_1$ or $X_2$ is a direct linkage, L may be a condensed cyclic group having two six-membered rings and one five-membered ring condensed together. When neither of $X_1$ and $X_2$ is a direct linkage, L may be a condensed cyclic group having three six-membered rings condensed together.

In Formula 2, $R_4$ to $R_9$ may each independently be a hydrogen atom, a deuterium atom, a halogen atom, a cyano group, $SiR_{21}R_{22}$, $OR_{23}$, $SR_{24}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In Formula 2, $R_{17}$ to $R_{24}$ may each independently be a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

The polycyclic compound according to an example embodiment includes an isophthalonitrile derivative as an electron donor, a nitrogen-containing group as an electron acceptor, and a condensed cyclic group as a linker. The polycyclic compound may minimize the overlap of the highest occupied molecular orbital (HOMO) and the lowest unoccupied molecular orbital (LUMO) by substituting the electron acceptor moiety and the electron donor moiety into the same ring of the linker. Accordingly, an absolute value (Est) of a difference between a singlet energy level (S1) and a triplet energy level (T1) may decrease and a rate constant of reverse intersystem crossing (RISC) transforming the triplet energy level (T1) into the singlet energy level (S1) may increase, and the efficiency of an organic electroluminescence device may be improved. In addition, according to the increase of the reverse intersystem crossing (RISC) rate, the concentration of triplet excitons may be restrained, efficiency degradation under high luminance (roll-off) which may arise by the interaction between a plurality of excitons (interaction between exciton-exciton) or the interaction between exciton-charge (hole or electron) (interaction between exciton-plaron), may be restrained, and an organic electroluminescence device having high efficiency may be provided.

In an example embodiment, Formula 1 may be represented by the following Formula 3:

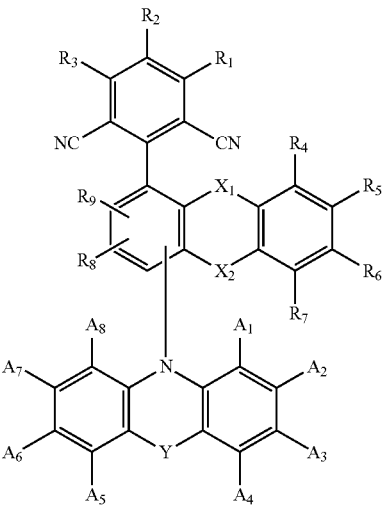

[Formula 3]

In Formula 3, Y, $A_1$ to $A_8$, $X_1$, $X_2$, and $R_1$ to $R_9$ are the same as defined in Formula 1 and Formula 2. Formula 3 represents an example embodiment of a case where a nitrogen-containing group and an isophthalonitrile derivative are substituted into one ring, i.e., a same ring, of the linker.

In an example embodiment, Formula 3 may be represented by any one among the following Formula 3-1 to Formula 3-3:

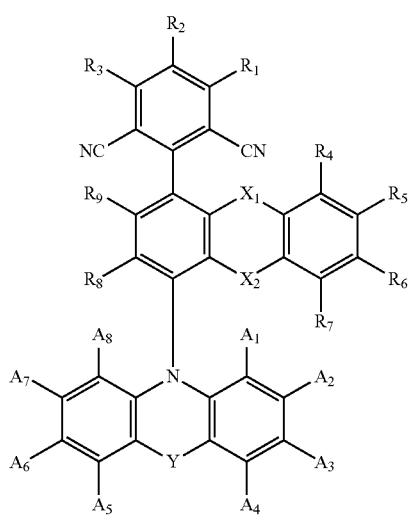

[Formula 3-1]

[Formula 3-2]

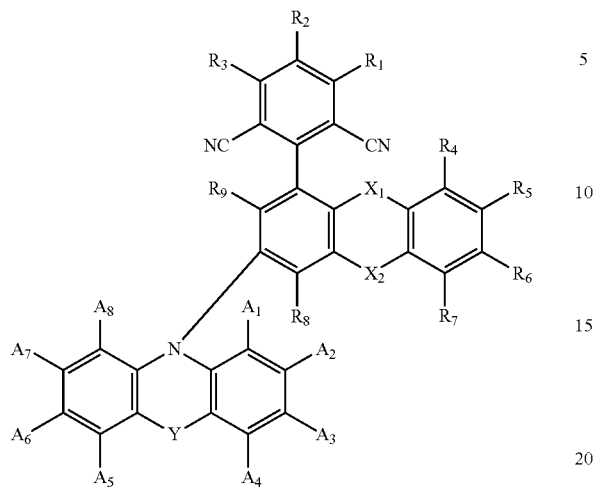

[Formula 3-3]

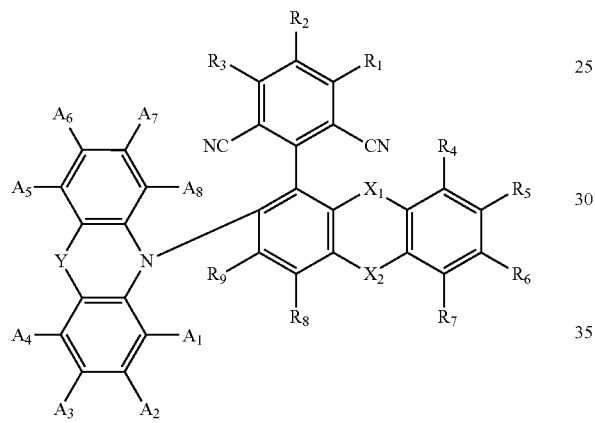

In Formula 3-1 to Formula 3-3, Y, $A_1$ to $A_8$, $X_1$, $X_2$, and $R_1$ to $R_9$ are the same as defined in Formula 1 and Formula 2.

Formula 3-1 represents an example embodiment of a case where the nitrogen-containing group and the isophthalonitrile derivative are substituted into para position, Formula 3-2 represents an example embodiment of a case where the nitrogen-containing group and the isophthalonitrile derivative are substituted into meta position, and Formula 3-3 represents an example embodiment of a case where the nitrogen-containing group and the isophthalonitrile derivative are substituted into ortho position.

In an example embodiment, Formula 3 may be a group represented by Formula 3-2. In the polycyclic compound, the nitrogen-containing group and the isophthalonitrile derivative may be substituted into the same ring of the linker in meta position.

In Formula 1, $R_1$ and $R_3$ of Formula 1 may each independently be a hydrogen atom, and $R_2$ of Formula 1 may be a hydrogen atom, a cyano group, $SiR_{14}R_{15}$, $SR_{16}$, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In an example embodiment, Formula 3 may be represented by any one among the following Formula 4-1 to Formula 4-3:

[Formula 4-1]

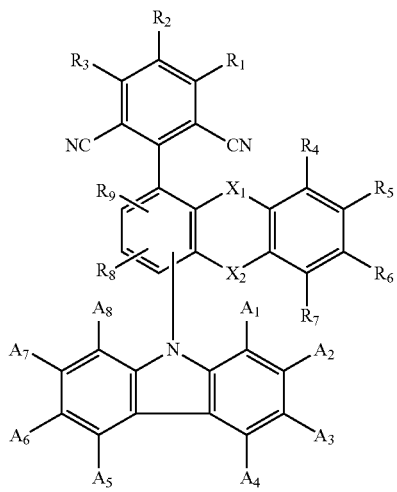

[Formula 4-2]

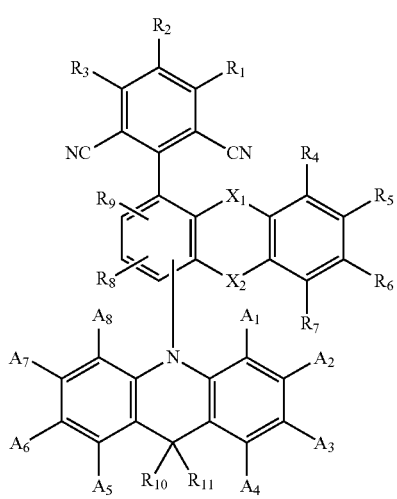

[Formula 4-3]

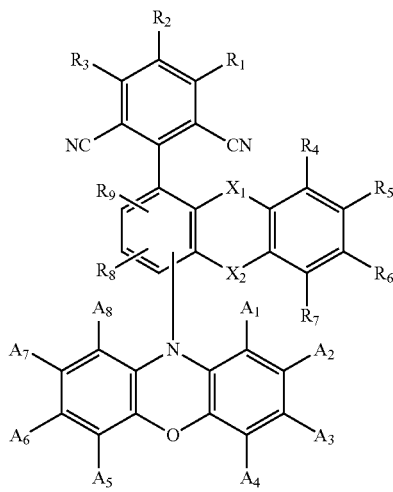

In Formula 4-1 to Formula 4-3, $A_1$ to $A_8$, $X_1$, $X_2$, and $R_1$ to $R_{11}$ are the same as defined in Formula 1 and Formula 2.

Formula 4-1 represents an example embodiment of a case where Y is a direct linkage, Formula 4-2 represents an example embodiment of a case where Y is $CR_{10}R_{11}$, and Formula 4-3 represents an example embodiment of a case where Y is O.

The polycyclic compound represented by Formula 1 may be a material for emitting delayed fluorescence. The polycyclic compound of an example embodiment may be a material for a thermally activated delayed fluorescence.

The polycyclic compound represented by Formula 1 may have an absolute value (Est) of a difference between a singlet energy level (S1) and a triplet energy level (T1) of about 0.1 eV or less. For example, S1−T1=0.1 eV.

For example, the polycyclic compound represented by Formula 1 may have a small difference between a singlet energy level (S1) and a triplet energy level (T1), and may be used as a material for emitting thermally activated delayed fluorescence. For example, the polycyclic compound represented by Formula 1 may be used as a blue emitting material emitting thermally activated delayed fluorescence. The polycyclic compound of an example embodiment may be a material for thermally activated delayed fluorescence, and emitting green light or red light.

The polycyclic compound represented by Formula 1 may be any one among the compounds represented in the following Compound Group 1:

[Compound Group 1]

1
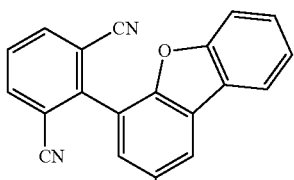

2
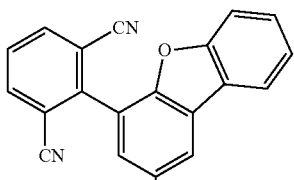

3
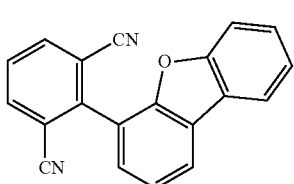

4
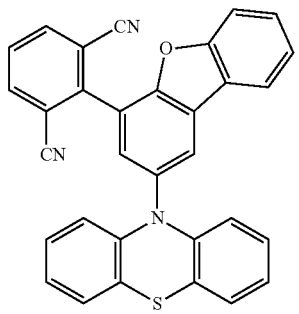

5
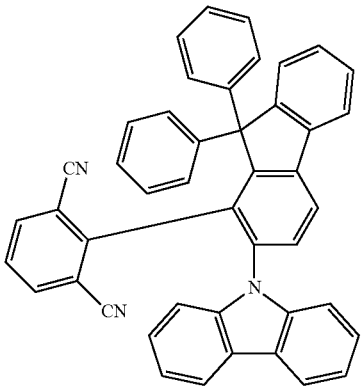

6
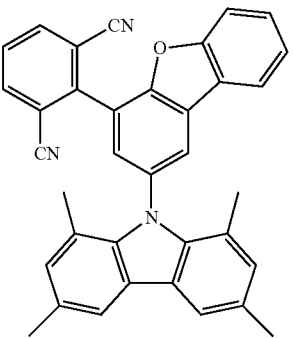

7
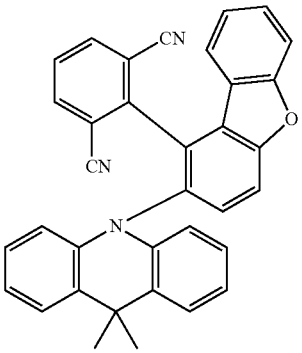

-continued
8
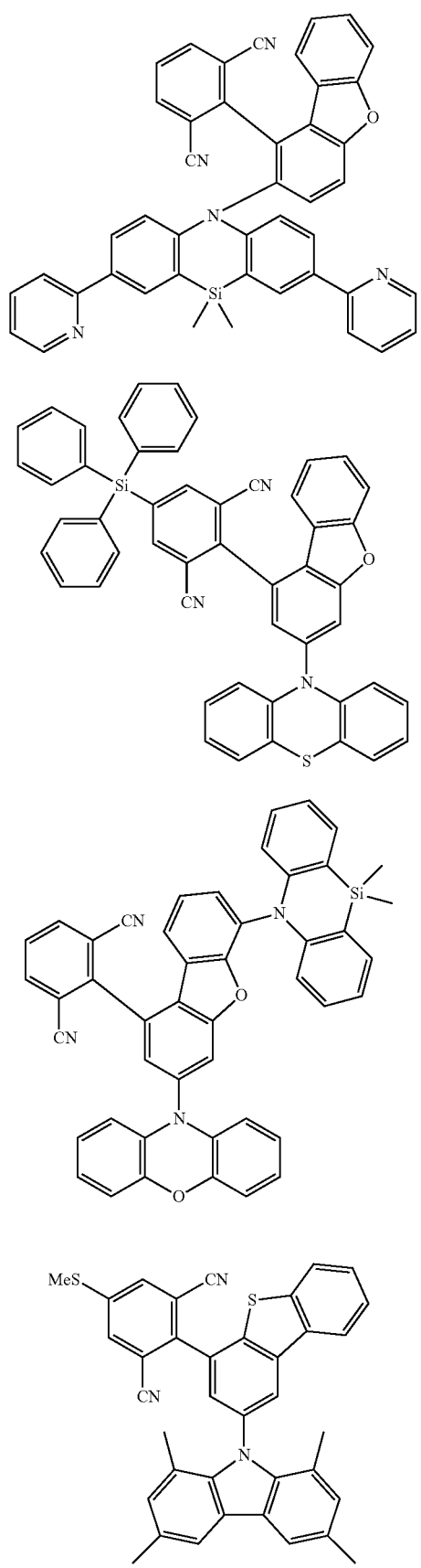
9
10
11
-continued
5
12
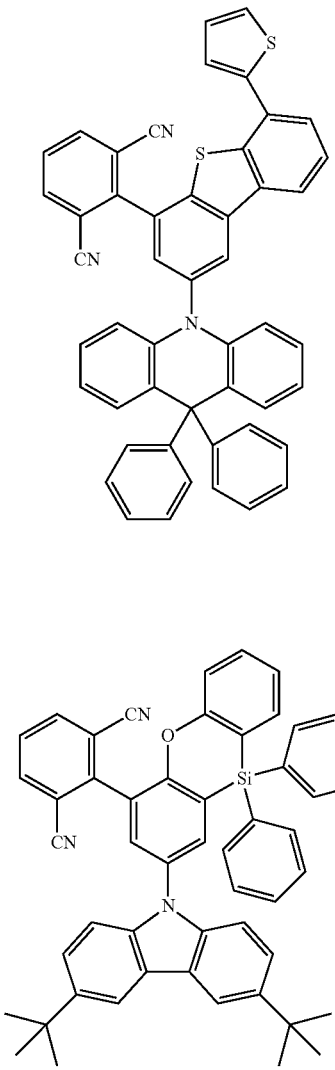
13
14
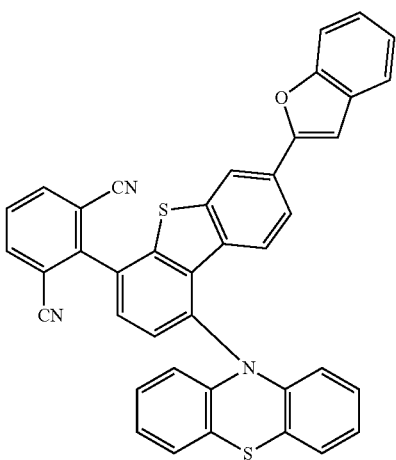

-continued
15
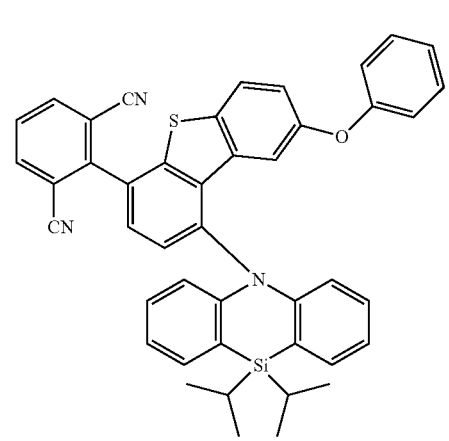
16
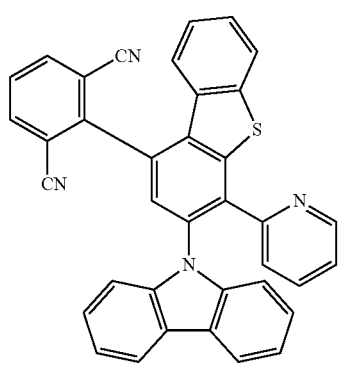
17
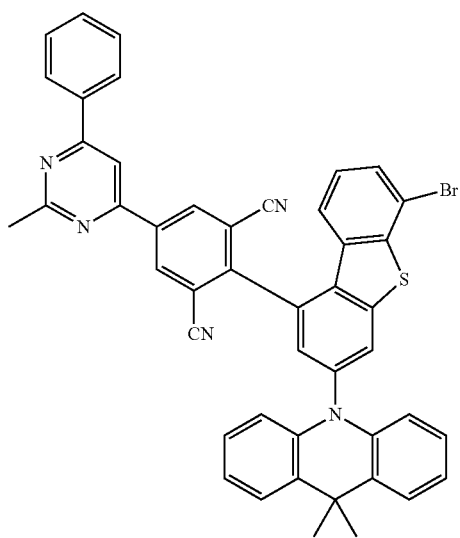
-continued
18
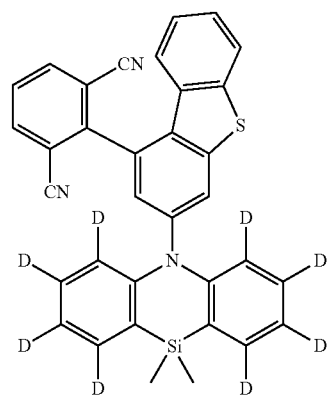
19
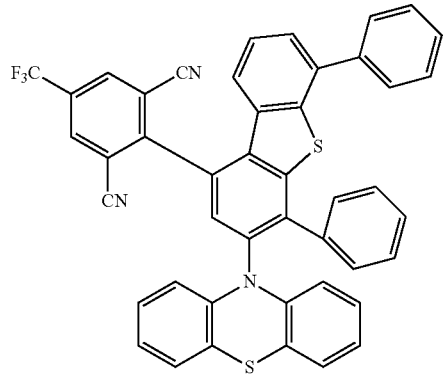
20
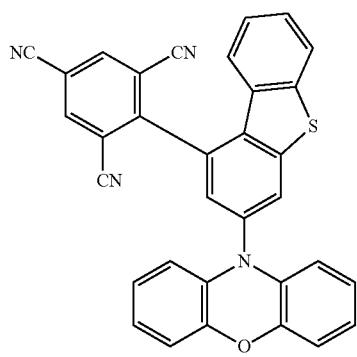
21
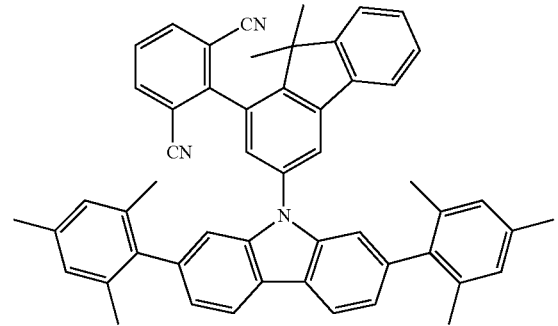

22
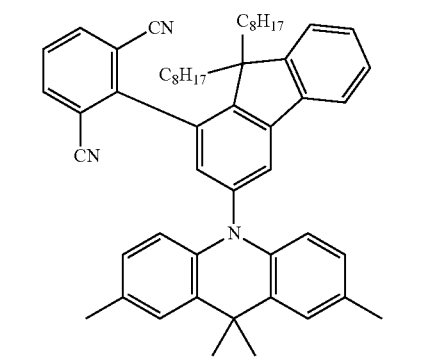
23
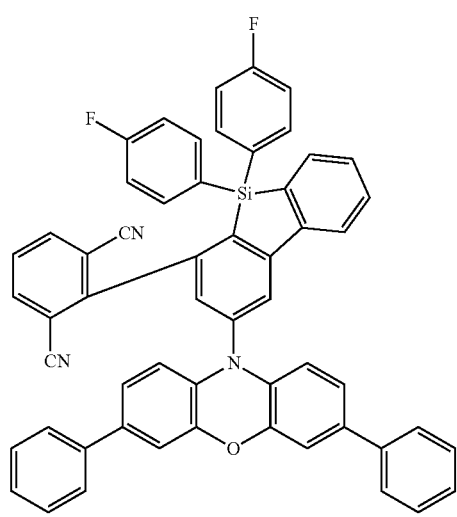
24
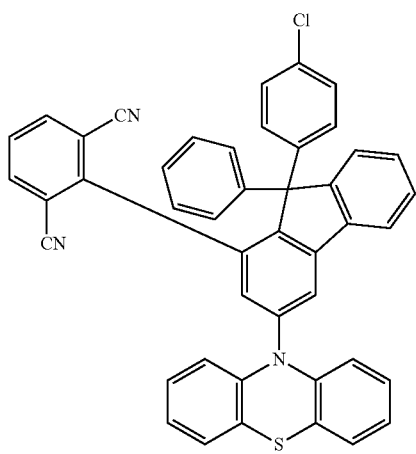
25
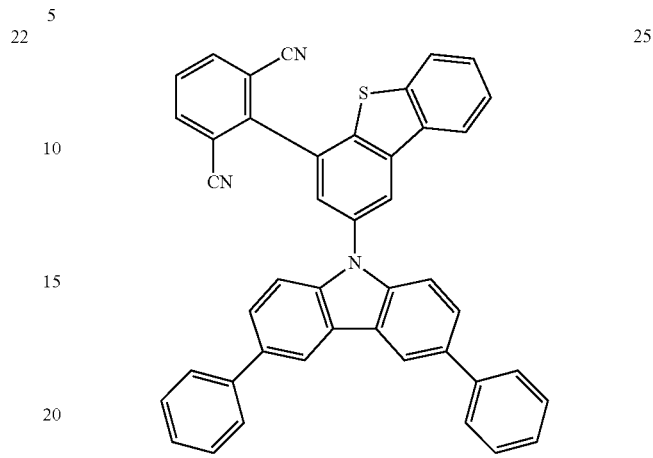
26
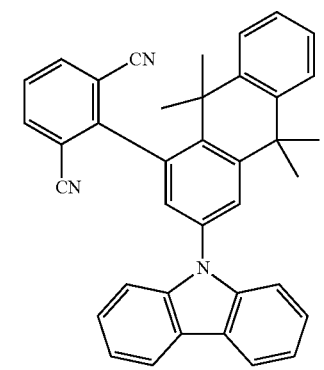
27
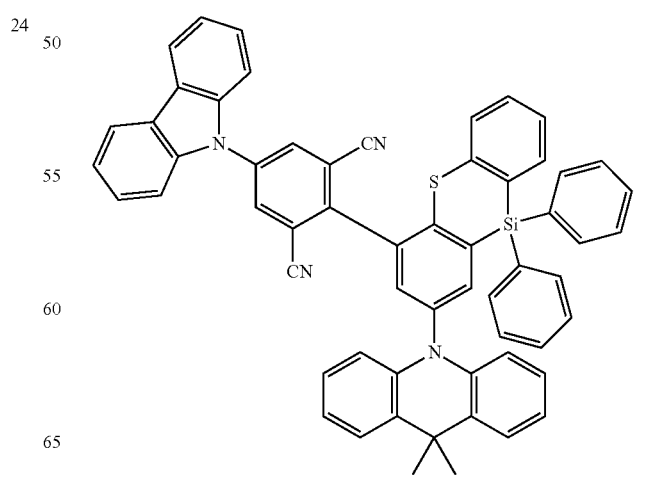

-continued
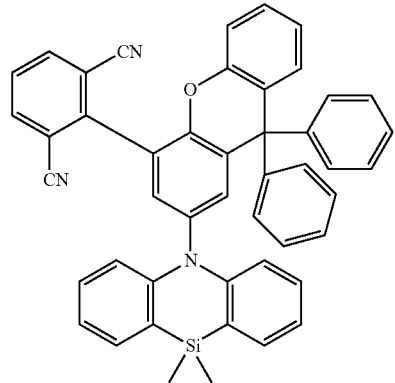
28
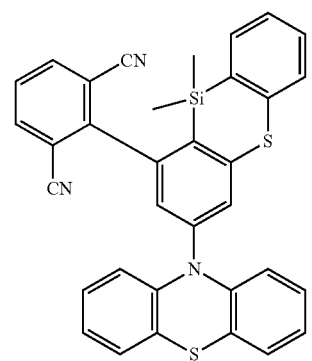
29
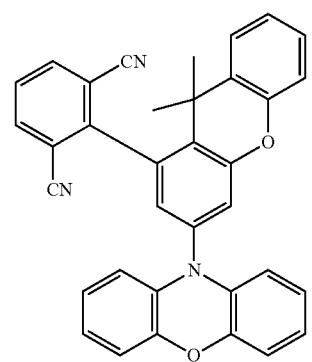
30
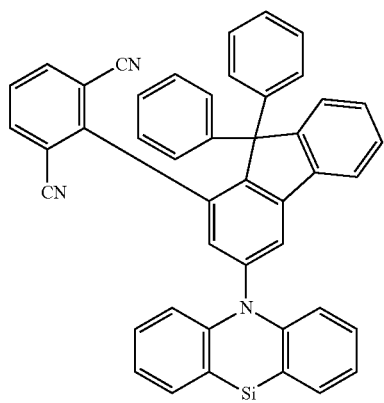
31
-continued
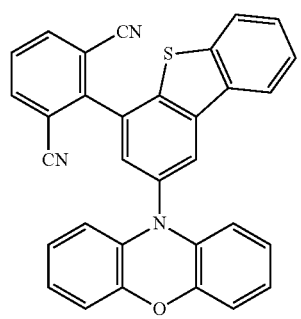
32
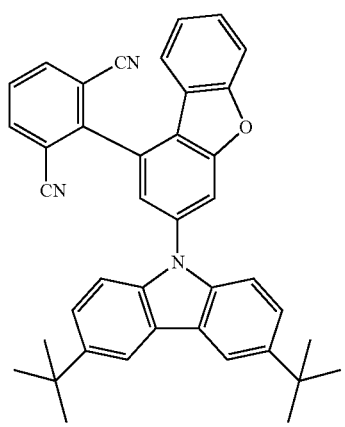
33
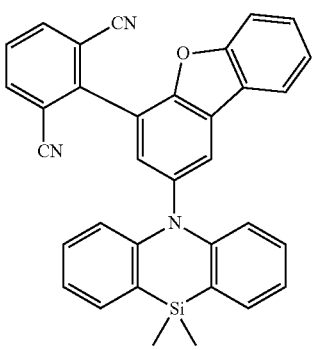
34
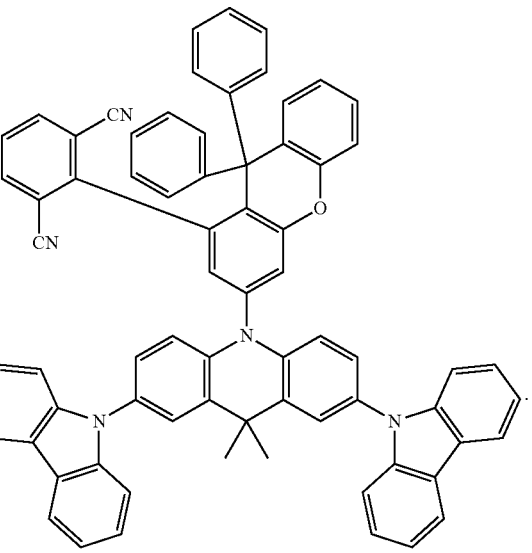
35

The polycyclic compound represented by Formula 1 may be used in an organic electroluminescence device 10 of an example embodiment, and may improve the efficiency and life of the organic electroluminescence device and restrain the roll-off phenomenon. For example, the polycyclic compound represented by Formula 1 may be used in the emission layer EML of an organic electroluminescence device 10 of an example embodiment, and may improve the emission efficiency and life of the organic electroluminescence device and restrain roll-off.

According to an example embodiment, a polycyclic compound includes one electron donor moiety, one electron acceptor moiety, and a linker connecting the electron donor moiety and the electron acceptor moiety in one compound unit, and an isophthalonitrile derivative which is the electron donor moiety and a nitrogen-containing group which is an electron acceptor moiety are substituted into one ring of the linker. In the polycyclic compound according to an example embodiment, the difference between singlet energy and triplet energy may be minimized, and thus, the polycyclic compound may be used as a blue emitting material that emits be thermally activated delayed fluorescence. In addition, the overlap of LUMO and HOMO may be minimized, and the polycyclic compound may be used as a light-emitting material which may restrain roll-off.

In an example embodiment, the emission layer EML includes a host and a dopant, and the host may be a host for emitting delayed fluorescence and the dopant may be a dopant for emitting delayed fluorescence. The polycyclic compound represented by Formula 1 may be included as a dopant material of an emission layer EML. For example, the polycyclic compound represented by Formula 1 may be used as a TADF dopant.

In an example embodiment, the emission layer EML may include a suitable host material. For example, in an example embodiment, the emission layer EML may include as a host material, tris(8-hydroxyquinolino)aluminum (Alq3), 4,4'-bis(N-carbazolyl)-1,1'-biphenyl (CBP), poly(N-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetrasiloxane (DPSiO$_4$), 2,8-bis(diphenylphosphoryl)dibenzofuran (PPF), etc. Any known host materials for emitting delayed fluorescence other than the suggested host materials may be included.

In the organic electroluminescence device 10 of an example embodiment, the emission layer EML may further include a suitable dopant material. In an example embodiment, the emission layer EML may include as a dopant, styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

Referring to FIGS. 1 to 3 again, in the organic electroluminescence device 10 of an example embodiment, the electron transport region ETR may be provided on the emission layer EML. The electron transport region ETR may include at least one of a hole blocking layer, an electron transport layer ETL or an electron injection layer EIL.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure having a plurality of different materials, or a structure laminated from the first electrode EL1 of electron transport layer ETL/electron injection layer EIL, or hole blocking layer/electron transport layer ETL/electron injection layer EIL. The thickness of the electron transport region ETR may be, for example, from about 100 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

When the electron transport region ETR includes an electron transport layer ETL, the electron transport region ETR may include, for example, tris(8-hydroxyquinolinato) aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di (naphthalene-2-yl)anthracene (ADN), or a mixture thereof.

When the electron transport region ETR includes the electron transport layer ETL, the thickness of the electron transport layer ETL may be from about 100 Å to about 1,000 Å and may be, for example, from about 150 Å to about 500 Å. When the thickness of the electron transport layer ETL satisfies the above-described range, satisfactory electron transport properties may be obtained without substantial increase of a driving voltage.

When the electron transport region ETR includes the electron injection layer EIL, the electron transport region ETR may include, for example, LiF, lithium quinolate (LiQ), Li$_2$O, BaO, NaCl, CsF, a metal in lanthanides such as Yb, or a metal halide such as RbCl, RbI, and KI. The electron injection layer EIL also may be formed using a mixture material of an electron transport material and an insulating organometal salt. The organometal salt may be a material having an energy band gap of about 4 eV or more. For example, the organometal salt may include, for example, metal acetates, metal benzoates, metal acetoacetates, metal acetylacetonates, or metal stearates.

When the electron transport region ETR includes the electron injection layer EIL, the thickness of the electron injection layer EIL may be from about 1 Å to about 100 Å, and from about 3 Å to about 90 Å. When the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer may include, for example, at least one of 2,9-dimethyl-4,7-diphenyl-1,10-phenanthroline (BCP), or 4,7-diphenyl-1,10-phenanthroline (Bphen).

The second electrode EL2 may be provided on the electron transport region ETR. The second electrode EL2 may have conductivity, and may be formed using a metal alloy or a conductive compound. The second electrode EL2 may be a cathode. The second electrode EL2 may be a transmissive electrode, a transflective electrode or a reflective electrode. When the second electrode EL2 is the transmissive electrode, the second electrode EL2 may include a transparent metal oxide, for example, ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

The second electrode EL2 may be connected with an auxiliary electrode. When the second electrode EL2 is connected with the auxiliary electrode, the resistance of the second electrode EL2 may be decreased.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes may recombine in the emission layer EML to produce excitons, and the excitons may emit light via transition from an excited state to a ground state.

When the organic electroluminescence device 10 is a top emission type, the first electrode EL1 may be a reflective electrode and the second electrode EL2 may be a transmissive electrode or a transflective electrode. When the organic electroluminescence device 10 is a bottom emission type, the first electrode EL1 may be a transmissive electrode or a transflective electrode and the second electrode EL2 may be a reflective electrode.

The organic electroluminescence device of an example embodiment may use the polycyclic compound as a material for an emission layer, and may have improved light-emitting efficiency and life characteristics and restrain roll-off phenomenon.

An example embodiment provides a polycyclic compound represented by the following Formula 1:

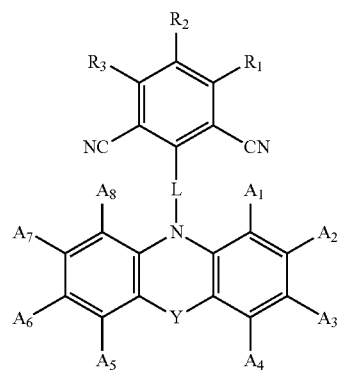

[Formula 1]

In Formula 1, Y may be $CR_{10}R_{11}$, $SiR_{12}R_{13}$O, S, or a direct linkage.

In Formula 1, $R_1$ to $R_3$ may each independently be a hydrogen atom, a deuterium atom, a halogen atom, a cyano group, $SiR_{14}R_{15}$, $SR_{16}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In Formula 1, $A_1$ to $A_8$ and $R_{10}$ to $R_{16}$ may each independently be a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

The linker L may be represented by the following Formula 2:

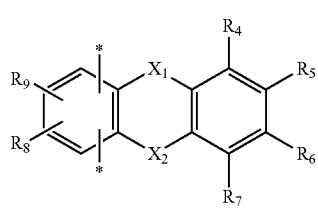

[Formula 2]

In Formula 2, $X_1$ and $X_2$ may each independently be a direct linkage, $CR_{17}R_{18}$, $SiR_{19}R_{20}$, O, or S. In an implementation, $X_1$ and $X_2$ may not both be direct linkages at the same time. When $X_1$ or $X_2$ is a direct linkage, L may be a condensed cyclic group that includes two six-membered rings and one five-membered ring condensed together. When both $X_1$ and $X_2$ are not direct linkages, L may be a condensed cyclic group that includes three six-membered rings condensed together.

In Formula 2, $R_4$ to $R_9$ may each independently be a hydrogen atom, a deuterium atom, a halogen atom, a cyano group, $SiR_{21}R_{22}$, $OR_{23}$, $SR_{24}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In Formula 2, $R_{17}$ to $R_{24}$ may each independently be a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

The same explanation on the polycyclic compound in the organic electroluminescence device of an example embodiment may be applied to the polycyclic compound of an example embodiment, represented by Formula 1.

The polycyclic compound according to an example embodiment may be any one selected from the compounds represented in Compound Group 1 above.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

1. Synthesis of Polycyclic Compounds

Synthetic methods of the polycyclic compounds according to example embodiments will be particularly explained for Compound 2, Compound 3, Compound 6, Compound 13, and Compound 25.

Synthetic Example of Compound 2

1. Synthesis of Intermediate A-1

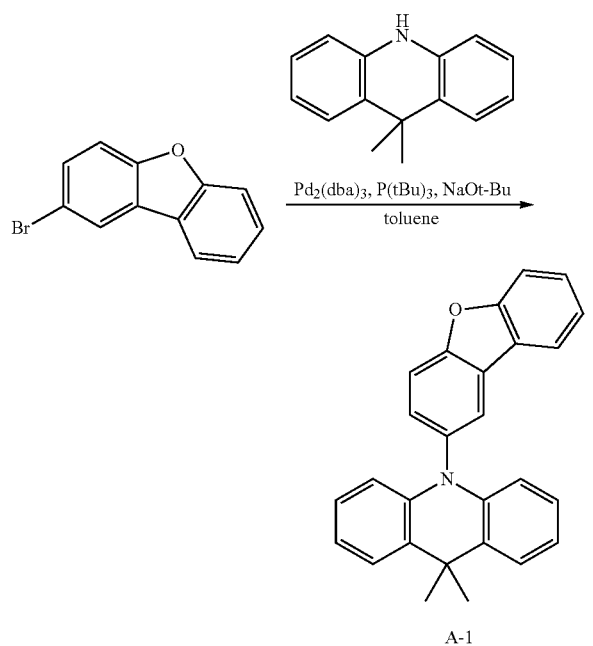

Intermediate A-1 was synthesized by the procedure described below.

Under an argon atmosphere, to a 200 ml, three-neck flask, 8.0 g of 2-bromodibenzofuran, 11.8 g of 9,10-dihydro-9,9-dimethylacridine, 1.8 g of tris(dibenzylideneacetone)dipalladium, 3.8 g of P(tBu)₃, and 7.3 g of tBuONa were added, and then heated and refluxed in 83 ml of a toluene solvent for about 8 hours. After cooling in the air, water was added, and organic layers were separately taken, and solvents were removed by distillation. The crude product thus obtained was separated by silica gel column chromatography (using a mixture solvent of toluene and hexane) and recrystallized using hexane and toluene to obtain 11.5 g (yield 80%) of a target material as a white solid.

The molecular weight of the target material as measured by FAB-MS was 375.47. From the result, the target product was identified as Intermediate A-1.

2. Synthesis of Intermediate A-2

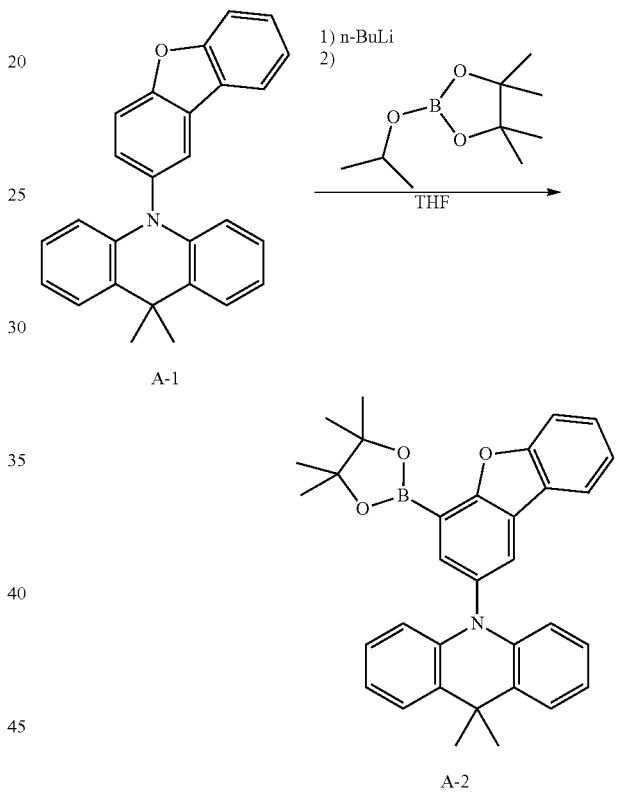

Intermediate A-2 was synthesized by the procedure described below.

Under an argon atmosphere, to a 100 ml, three-neck flask, 10.0 g of Intermediate A-1 was added and stirred in 61 ml of a THF solvent at about −78° C. After that, 25 ml of n-BuLi was added thereto and stirring was performed for about 2 hours. Then, 5.2 g of 2-isopropoxy-4,4,5,5-tetramethyl-1,3,2-dioxaborolane was added, followed by stirring at room temperature for about 4 hours. After that, water was added to the reaction product, and organic layers were separately taken, and solvents were removed by distillation. The crude product thus obtained was recrystallized using dichloromethane and methanol to obtain 10.6 g (yield 79%) of a target material as a white solid. The molecular weight of the target material as measured by LC-MS was 501.43. From the result, the target product was identified as Intermediate A-2.

3. Synthesis of Final Product Compound 2

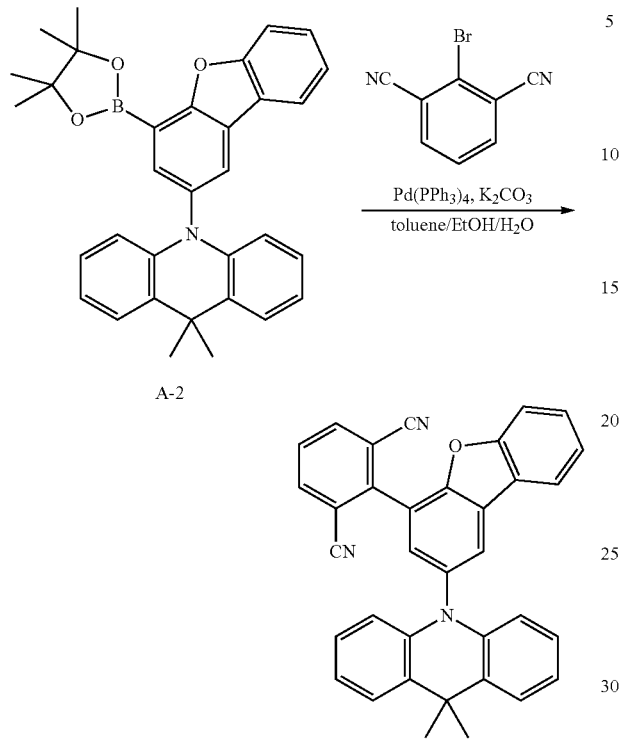

Compound 2 was synthesized by the procedure described below.

Under an argon atmosphere, to a 100 ml, three-neck flask, 2.5 g of Intermediate A-2, 1.0 g of 2-bromoisophthalonitrile, 0.3 g of tetrakis(triphenylphosphine)palladium, and 1.4 g of $K_2CO_3$ were added, and was heated and refluxed in a mixture solvent of 100 ml of toluene, 2 ml of ethanol and 4 ml of water, for about 7 hours. After that, water was added to the reaction product, and organic layers were separately taken, and solvents were removed by distillation. The crude product thus obtained was separated by silica gel column chromatography (using a mixture solvent of toluene and hexane) and recrystallized using hexane and toluene to obtain 2.0 g (yield 79%) of a target material as a white solid.

The molecular weight of the target material as measured by FAB-MS was 501.59. From the result, the target product was identified as Compound 2. Compound 2 thus obtained was separated via sublimation by a train-sublimation system, and then was used for the manufacture of an organic EL device.

Synthetic Example of Compound 3

1. Synthesis of Intermediate B-1

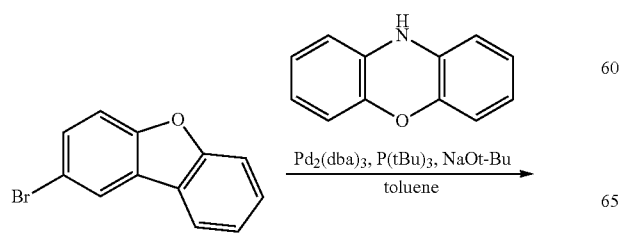

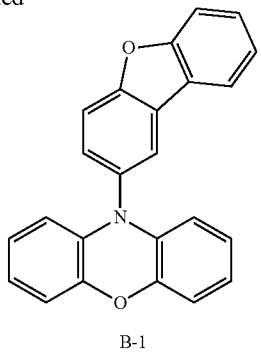

The final target Intermediate B-1 was obtained with a yield of 76% by performing the same procedure for synthesizing Intermediate A-1 except for using phenoxazine instead of 9,10-dihydro-9,9-dimethylacridine.

The molecular weight of Intermediate B-1 as measured by FAB-MS was 349.39.

2. Synthesis of Intermediate B-2

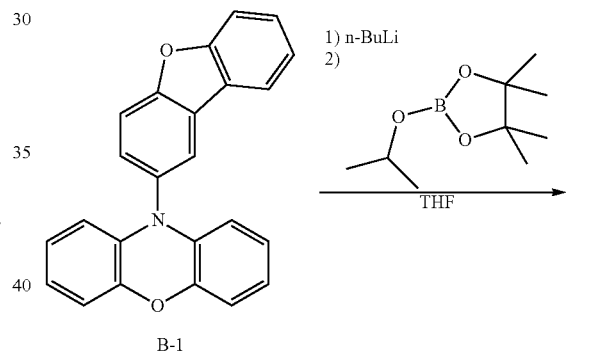

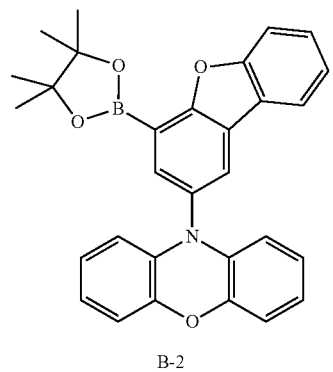

The final target Compound B-2 was obtained with a yield of 65% by performing the same procedure for synthesizing Intermediate A-2 except for using Intermediate B-1 instead of Intermediate A-1.

The molecular weight of final target Intermediate B-2 as measured by FAB-MS was 475.35.

3. Synthesis of Final Product Compound 3

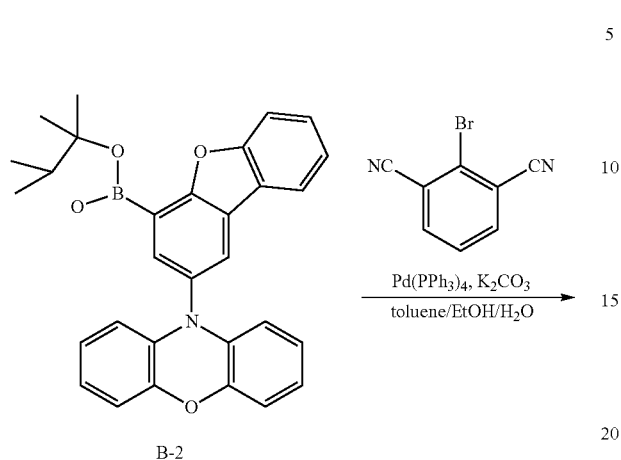

B-2

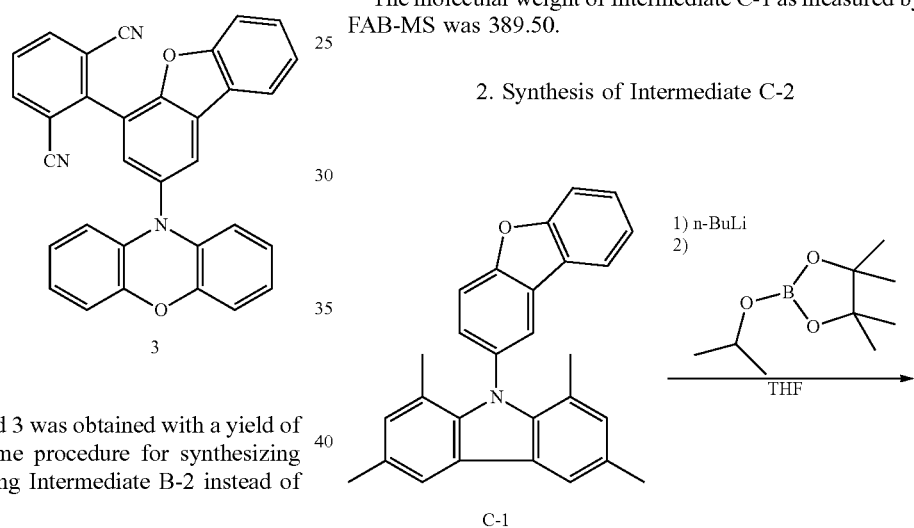

3

The final target Compound 3 was obtained with a yield of 88% by performing the same procedure for synthesizing Compound 2 except for using Intermediate B-2 instead of Intermediate A-2.

The molecular weight of Compound 3 as measured by FAB-MS was 475.51.

Synthetic Example of Compound 6

1. Synthesis of Intermediate C-1

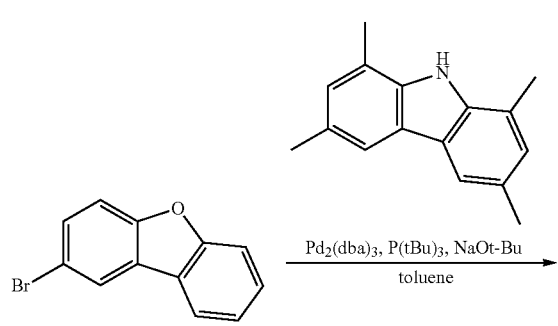

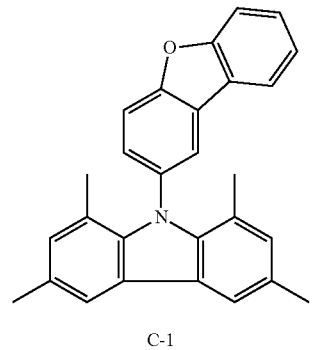

C-1

The final target Intermediate C-1 was obtained with a yield of 70% by performing the same procedure for synthesizing Intermediate A-1 except for using 1,3,6,8-tetramethylcarbazole instead of 9,10-dihydro-9,9-dimethylacridine.

The molecular weight of Intermediate C-1 as measured by FAB-MS was 389.50.

2. Synthesis of Intermediate C-2

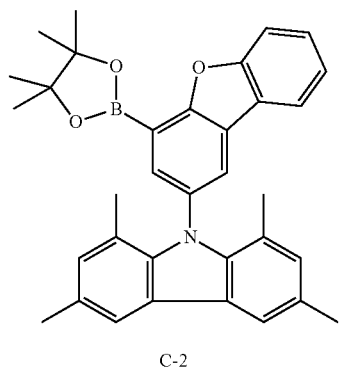

C-2

The final target Intermediate C-2 was obtained with a yield of 75% by performing the same procedure for synthesizing Intermediate A-2 except for using Intermediate C-1 instead of Intermediate A-1.

The molecular weight of Intermediate C-2 as measured by FAB-MS was 515.46.

3. Synthesis of Final Product Compound 6

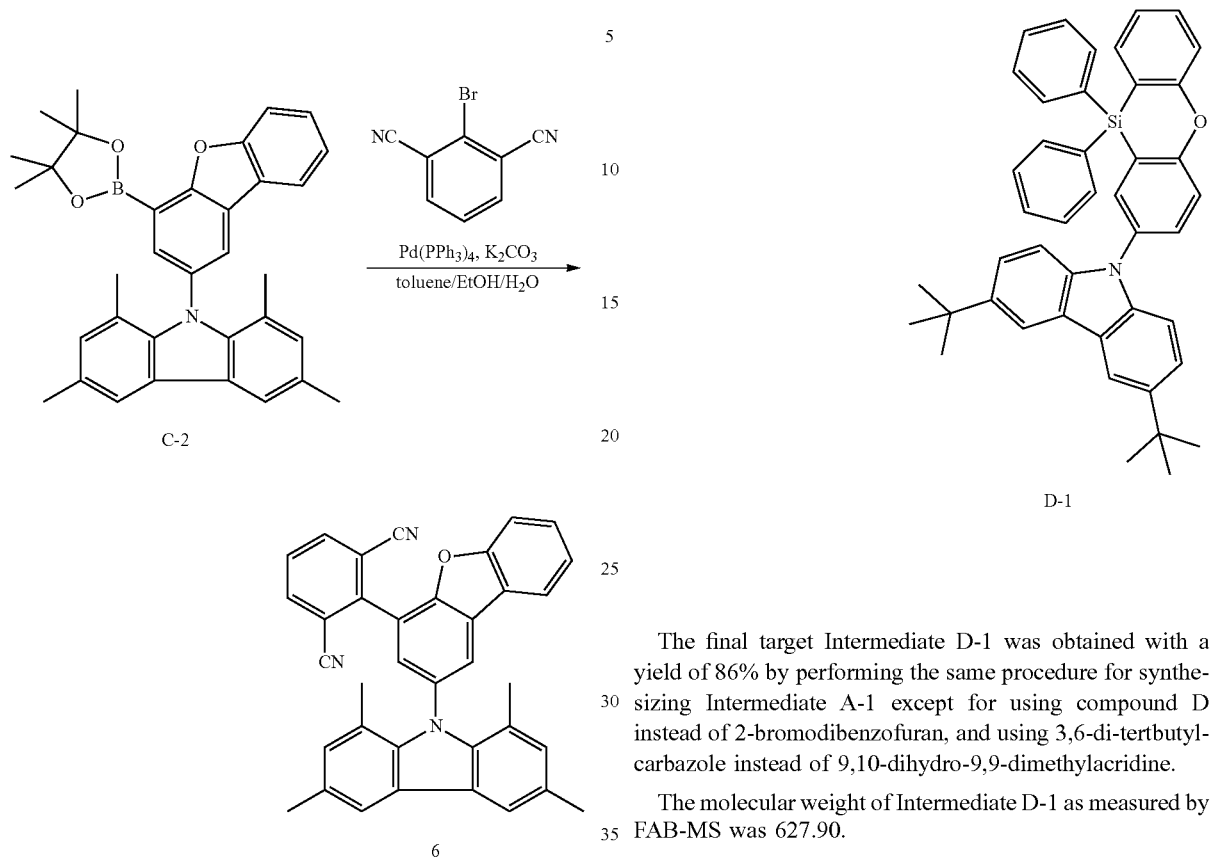

The final target Compound 6 was obtained with a yield of 88% by performing the same procedure for synthesizing Compound 2 except for using Intermediate C-2 instead of Intermediate A-2.

The molecular weight of Compound 6 as measured by FAB-MS was 475.51.

Synthetic Example of Compound 13

1. Synthesis of Intermediate D-1

The final target Intermediate D-1 was obtained with a yield of 86% by performing the same procedure for synthesizing Intermediate A-1 except for using compound D instead of 2-bromodibenzofuran, and using 3,6-di-tertbutyl-carbazole instead of 9,10-dihydro-9,9-dimethylacridine.

The molecular weight of Intermediate D-1 as measured by FAB-MS was 627.90.

2. Synthesis of Intermediate D-2

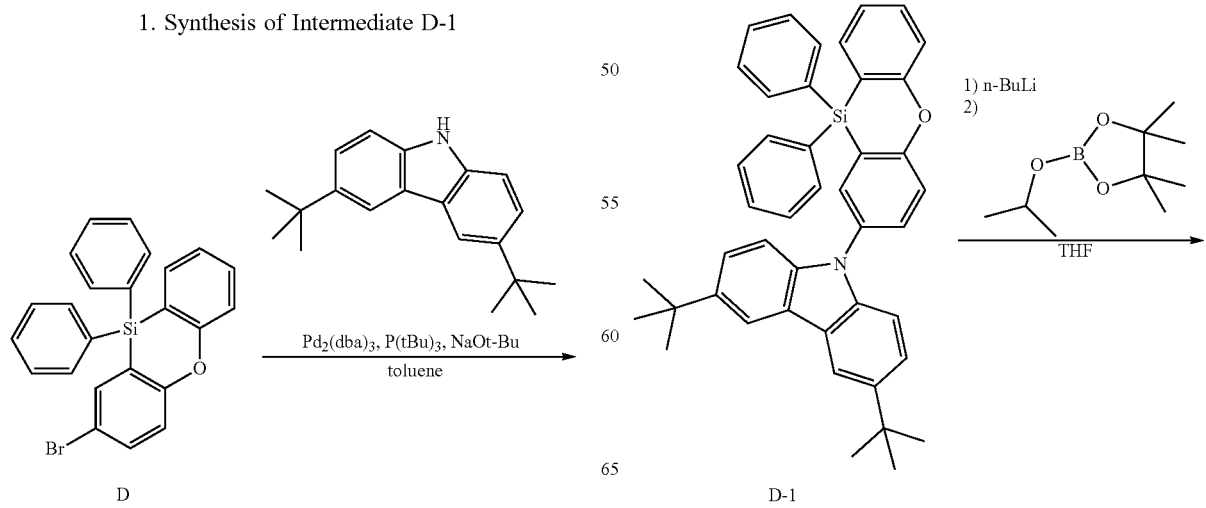

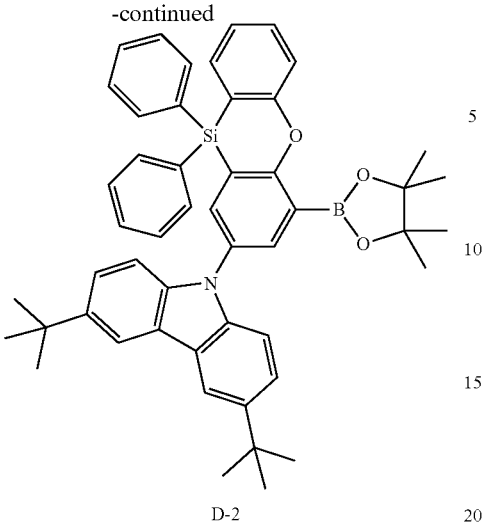

D-2

The final target Intermediate D-2 was obtained with a yield of 68% by performing the same procedure for synthesizing Intermediate A-2 except for using Intermediate D-1 instead of Intermediate A-1.

The molecular weight of Intermediate D-2 as measured by FAB-MS was 753.86.

3. Synthesis of Final Product Compound 13

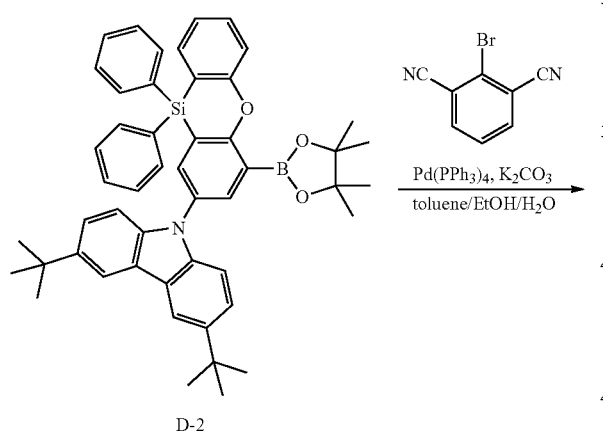

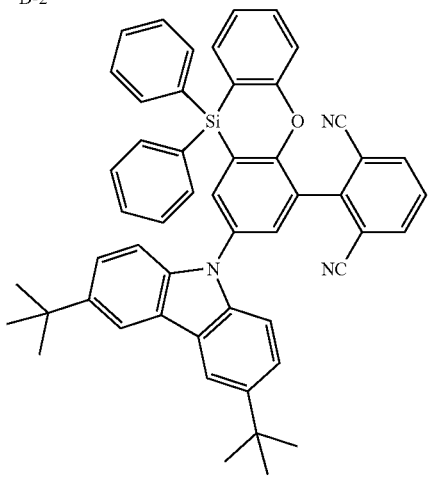

13

The final target Compound 13 was obtained with a yield of 78% by performing the same procedure for synthesizing Compound 2 except for using Intermediate D-2 instead of Intermediate A-2.

The molecular weight of Compound 13 as measured by FAB-MS was 754.02.

Synthetic Example of Compound 25

1. Synthesis of Intermediate E-1

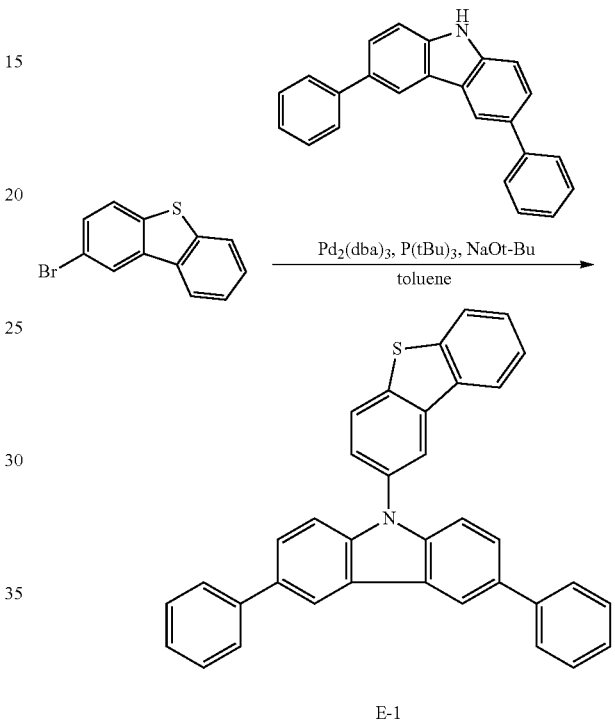

E-1

The final target Intermediate E-1 was obtained with a yield of 88% by performing the same procedure for synthesizing Intermediate A-1 except for using 2-bromodibenzothiophene instead of 2-bromodibenzofuran, and using 3,6-di-phenylcarbazole instead of 9,10-dihydro-9,9-dimethylacridine.

The molecular weight of Intermediate E-1 measured by FAB-MS was 501.65.

2. Synthesis of Intermediate E-2

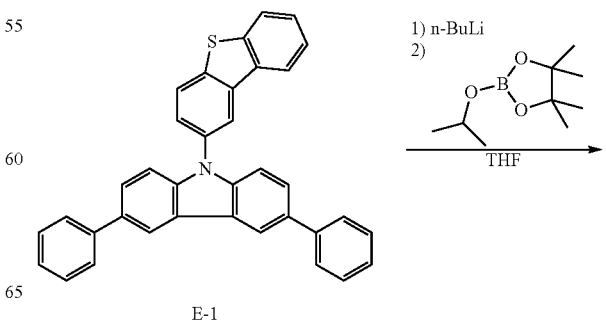

E-1

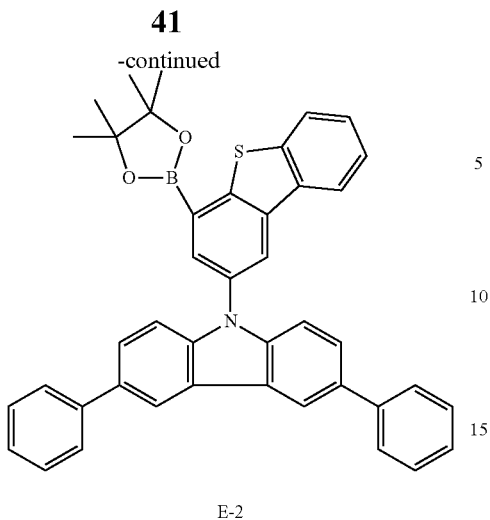

E-2

The final target Intermediate E-2 was obtained with a yield of 60% by performing the same procedure for synthesizing Intermediate A-2 except for using Intermediate E-1 instead of Intermediate A-1.

The molecular weight of Intermediate E-2 as measured by FAB-MS was 627.61.

3. Synthesis of Final Product Compound 25

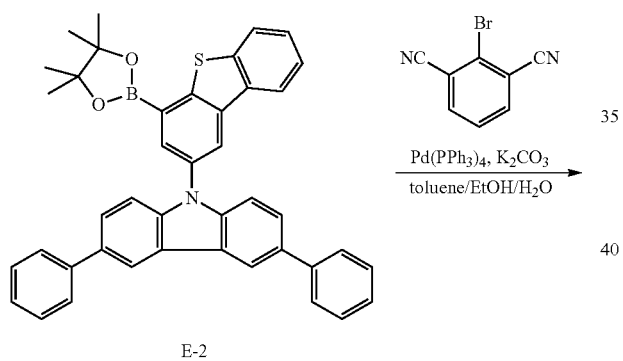

The final target Compound 25 was obtained with a yield of 69% by performing the same procedure for synthesizing Compound 2 except for using Intermediate E-2 instead of Intermediate A-2.

The molecular weight of Compound 25 as measured by FAB-MS was 627.76.

2. Manufacture and Evaluation of Organic Electroluminescence Device Including a Polycyclic Compound (Manufacture of Organic Electroluminescence Devices)

Organic electroluminescence devices were manufactured by a method described below.

Organic electroluminescence devices of Examples 1 to 5 were manufactured using the polycyclic compounds of Compound 2, Compound 3, Compound 6, Compound 13, and Compound 25, respectively, as materials for an emission layer. Compounds used in the emission layer in Examples 1 to 5 and Comparative Examples 1 to 5 are shown below.

TABLE 1

| Example Compounds |
| --- |

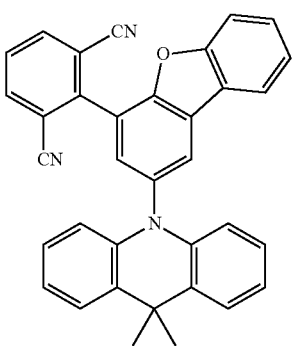 [SMILES: N#Cc1cccc(C#N)c1-c1cc(N2c3ccccc3Oc3ccccc32)cc2c1oc1ccccc12]

2

TABLE 1-continued
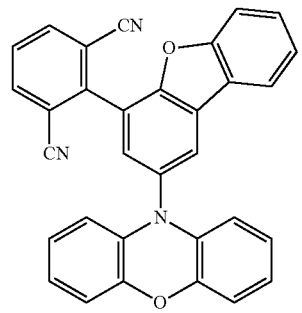
3
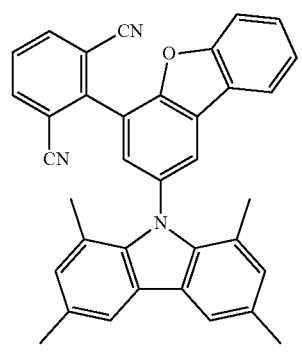
6
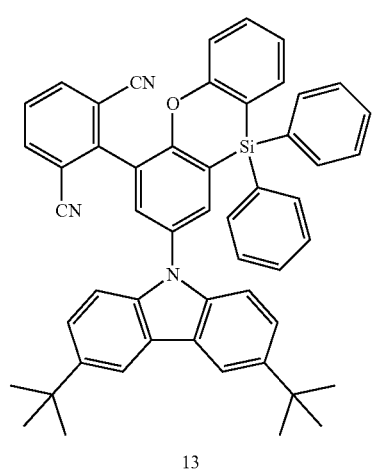 [SMILES: CC(C)(C)c1ccc2c(c1)c1cc(C(C)(C)C)ccc1n2-c1cc(-c2c(C#N)cccc2C#N)c2c(c1)[Si](c1ccccc1)(c1ccccc1)c1ccccc1O2]
13
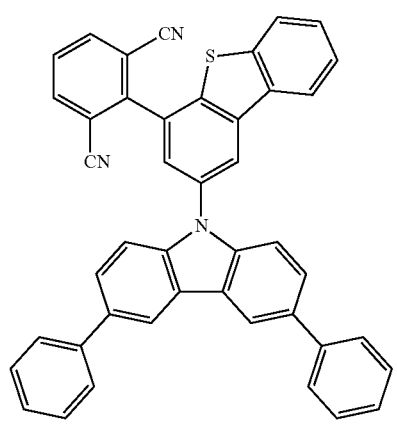
25

TABLE 1-continued
Comparative Compounds
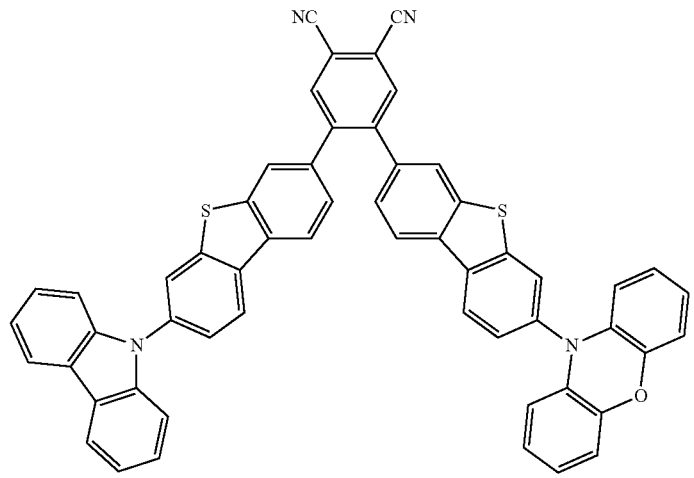
X-1
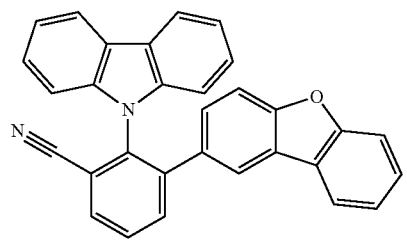
X-2
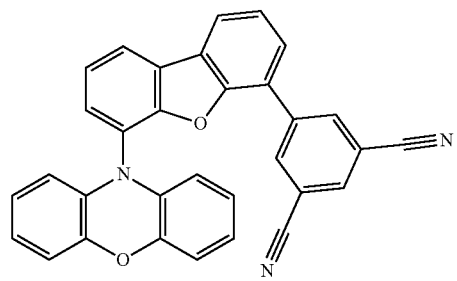
X-3
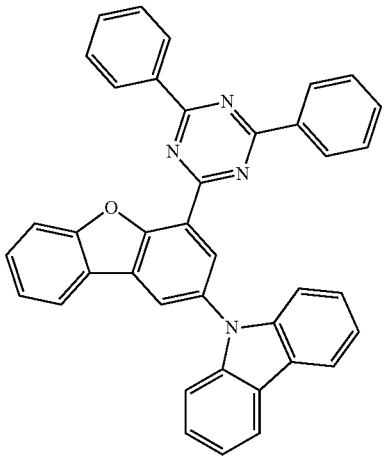
X-4

On a glass substrate, ITO was patterned to a thickness of about 1,500 Å and washed with ultra-pure water, and a UV ozone treatment was conducted for about 10 minutes. Then, HAT-CN was deposited to a thickness of about 100 Å, α-NPD was deposited to a thickness of about 800 Å, and mCP was deposited to a thickness of about 50 Å to form a hole transport region.

Then, a respective polycyclic compound of an Example/Comparative Example and DPEPO were co-deposited in a ratio of 24:76 to form an emission layer to a thickness of about 200 Å. In order to form the emission layer by the co-deposition, a respective Compound 2, 3, 6, 13, or 25 was mixed with DPEPO and deposited in Examples 1 to 5, and each of Comparative Compounds X-1, X-2, X-3, and X-4 was mixed with DPEPO and deposited in Comparative Examples 1 to 4.

Then, a layer with a thickness of about 100 Å was formed using DPEPO.

On the emission layer, a layer was formed using TPBi to a thickness of about 300 Å, and a layer was formed using LiF to a thickness of about 5 Å to form an electron transport region. Then, a second electrode was formed using aluminum (Al) to a thickness of about 1,000 Å.

In the examples, the hole transport region, the emission layer, the electron transport region, and the second electrode were formed by using a vacuum deposition apparatus.

(Energy Levels of Each Compound)

In Table 2 below, $\Delta E_{ST}$ (difference between a singlet energy level (S1 energy level, unit: eV), a triplet energy level (T1 energy level, unit: eV)), and charge separation degree (q amount) of Example Compounds 2, 3, 6, 13, and 25 and Comparative Compounds X-1, X-2, X-3, and X-4 are shown. The energy level values in Table 2 were calculated by a non-empirical molecular orbital method. For example, the energy level values were calculated using Gaussian 09 of Gaussian Co., using a functional of B3LYP and a basis function of 6-31 G(d). In addition, the contribution ratio of HOMO/LUMO of the donor moiety and the acceptor moiety of the example compounds were computed using Multiwfn and the charge separation degree (q amount) was computed.

TABLE 2

|  | $\Delta E_{ST}$ | q amount |
|---|---|---|
| Compound 2 | 0.0020 | 99.20 |
| Compound 3 | 0.0021 | 99.46 |
| Compound 6 | 0.0012 | 99.52 |
| Compound 13 | 0.082 | 98.84 |
| Compound 25 | 0.0062 | 99.04 |
| Comparative Compound X-1 | 0.0018 | 88.20 |
| Comparative Compound X-2 | 0.1074 | 77.80 |
| Comparative Compound X-3 | 0.0066 | 86.52 |
| Comparative Compound X-4 | 0.1650 | 69.4 |

(Evaluation of Properties of Organic Electroluminescence Device)

In order to evaluate the properties of the organic electroluminescence devices of the Examples and the Comparative Examples, the wavelength of maximum emission (nm), external quantum yield (%), and roll-off were evaluated. The wavelength of maximum emission was the greatest emission wavelength of emission spectrum at room temperature (about 300K). The measurement was conducted using a luminous brightness measurement apparatus, C9920-11 of HAMAMATSU Photonics Co. The roll-off was calculated by EQE (10 mA/cm$^2$)/EQE (max).

TABLE 3

| | Emission layer | Wavelength of maximum emission (nm) | External quantum yield (%) | Roll-off (%) |
|---|---|---|---|---|
| Example 1 | Compound 2 | 494 | 10.1 | 40 |
| Example 2 | Compound 3 | 512 | 12.3 | 32 |
| Example 3 | Compound 6 | 479 | 14.5 | 28 |
| Example 4 | Compound 13 | 473 | 15.4 | 39 |
| Example 5 | Compound 25 | 485 | 9.3 | 28 |
| Comparative Example 1 | Comparative Compound X-1 | 524 | 8.4 | 62 |
| Comparative Example 2 | Comparative Compound X-2 | 443 | 3.8 | 24 |
| Comparative Example 3 | Comparative Compound X-3 | 511 | 9.6 | 53 |
| Comparative Example 4 | Comparative Compound X-4 | 456 | 2.4 | 31 |

Referring to the results of Tables 2 and 3, it was found that the Example Compounds had a small $\Delta E_{ST}$ and showed high emission efficiency in a blue emission region at the same time.

All of example Compounds 2, 3, 6, 13, and 25 showed low $\Delta E_{ST}$ values of about 0.1 eV or less, and very high q amounts of about 98% or more. Accordingly, the polycyclic compound may be used as a material for thermally activated delayed fluorescence with high efficiency, thereby improving the emission efficiency of an organic electroluminescence device. In addition, the overlap of LUMO and HOMO in the polycyclic compounds may be minimized to improve a RISC rate and thus, the roll-off phenomenon of an organic electroluminescence device may be restrained.

In comparison, comparative Compounds X-1 and X-3 used in Comparative Example 1 and Comparative Example 3 showed low $\Delta E_{ST}$ values but q amounts of less than about 90%. Without being bound by theory, it is believed that because the electron acceptor moiety and the electron donor moiety of the compound were not substituted into the same ring, the overlap of LUMO and HOMO was high. Accordingly, the organic electroluminescence devices of Comparative Example 1 and Comparative Example 3 showed higher roll-off values than those of the Examples.

Comparative Compound X-2 used in Comparative Example 2 had a structure of directly connecting an electron acceptor moiety and an electron donor moiety without a linker, and had a relatively high $\Delta E_{ST}$ value and a low q amount of less than about 80%. Without being bound by theory, it is believed that comparative Compound X-2 did not act as a material for thermally activated delayed fluorescence. Thus, the organic electroluminescence device of Comparative Example 2 showed low external quantum efficiency.

Comparative Example X-4 used in Comparative Example 4 did not include an isophthalonitrile derivative as an electron acceptor, and had a relatively low $\Delta E_{ST}$ value and a low q amount of less than about 70%. Without being bound by theory, it is believed that comparative Compound X-4 did not act as a material for thermally activated delayed fluorescence. Thus, the organic electroluminescence device of Comparative Example 4 showed low external quantum efficiency.

By way of summation and review, to provide an organic electroluminescence device with high efficiency, techniques on phosphorescence emission, which uses energy in a triplet state, or delayed fluorescence emission, which uses the generating phenomenon of singlet excitons by the collision of triplet excitons (triplet-triplet annihilation, TTA), are being considered, and development of a material for thermally activated delayed fluorescence (TADF) using delayed fluorescence phenomenon is being considered.

An organic electroluminescence device according to an example embodiment may include a polycyclic compound (which includes an isophthalonitrile derivative, a linker, and a nitrogen-containing group, wherein the isophthalonitrile derivative and the nitrogen-containing group are substituted into the same ring of the linker) as a material for an emission layer, which may help provide high emission efficiency in a blue wavelength region and restrain roll-off.

An organic electroluminescence device according to an example embodiment may attain high efficiency and long life.

A polycyclic compound according to an example embodiment may improve the life and efficiency of an organic electroluminescence device and restrain roll-off.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic electroluminescence device, comprising:
a first electrode;
a hole transport region on the first electrode;
an emission layer on the hole transport region, the emission layer including a polycyclic compound;
an electron transport region on the emission layer; and
a second electrode on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and oxides thereof,
wherein:
the polycyclic compound includes an isophthalonitrile derivative, a linker, and a nitrogen-containing group,
each of the isophthalonitrile derivative and the nitrogen-containing group is substituted into a same ring of the linker, and
the linker is represented by the following Formula 2:

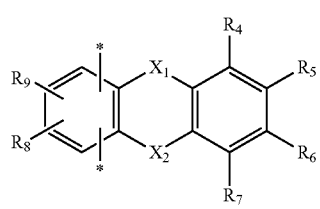

[Formula 2]

in Formula 2,
$X_1$ and $X_2$ are each independently a direct linkage, $CR_{17}R_{18}$, $SiR_{19}R_{20}$, O, or S, provided that $X_1$ and $X_2$ are not both the direct linkage, $R_4$ to $R_9$ are each independently a hydrogen atom, a deuterium atom, a halogen atom, a cyano group, $SiR_{21}R_{22}$, $OR_{23}$, $SR_{24}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and $R_{17}$ to $R_{24}$ are each independently a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

2. The organic electroluminescence device as claimed in claim 1, wherein the emission layer emits delayed fluorescence.

3. The organic electroluminescence device as claimed in claim 1, wherein:
the emission layer is a delayed fluorescence emission layer including a host and a dopant, and
the host is the polycyclic compound.

4. The organic electroluminescence device as claimed in claim 1, wherein the emission layer is a thermally activated delayed fluorescence emission layer that emits blue light.

5. The organic electroluminescence device as claimed in claim 1, wherein the polycyclic compound has an absolute value of a difference between a singlet energy level and a triplet energy level of about 0.1 eV or less.

6. The organic electroluminescence device as claimed in claim 1, wherein the polycyclic compound is represented by the following Formula 1:

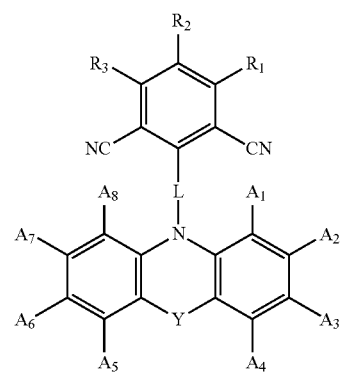

[Formula 1]

in Formula 1,
in the isophthalonitrile derivative, $R_1$ to $R_3$ are each independently a hydrogen atom, a deuterium atom, a halogen atom, a cyano group, $SiR_{14}R_{15}$, $SR_{16}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms,
in the nitrogen-containing group, Y is $CR_{10}R_{11}$, $SiR_{12}R_{13}$, O, S, or a direct linkage,
$A_1$ to $A_8$ and $R_{10}$ to $R_{16}$ are each independently a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and in the linker, L is represented by Formula 2 of claim 1.

7. The organic electroluminescence device as claimed in claim 6, wherein Formula 1 is represented by following Formula 3:

[Formula 3]

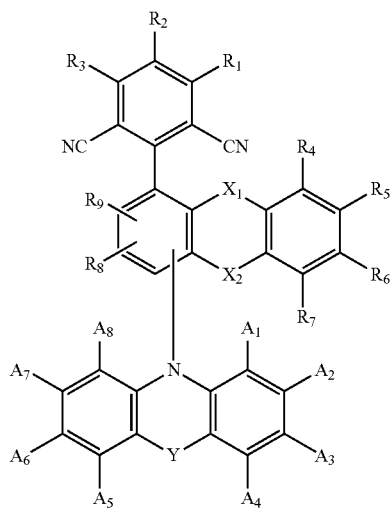

in Formula 3, Y, $A_1$ to $A_8$, $X_1$, $X_2$, and $R_1$ to $R_9$ are the same as defined in Formula 1 and Formula 2.

8. The organic electroluminescence device as claimed in claim 7, wherein Formula 3 is represented by any one among the following Formula 3-1 to Formula 3-3:

[Formula 3-1]

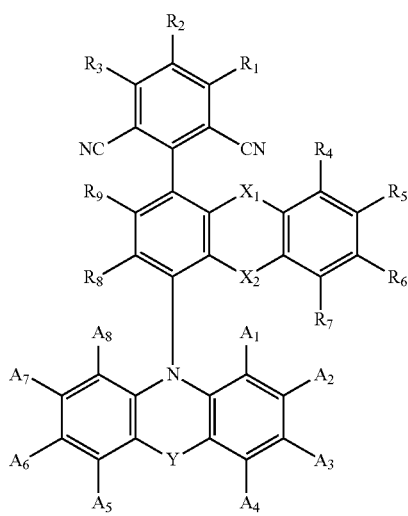

[Formula 3-2]

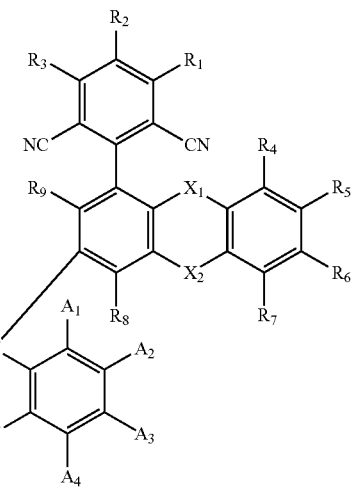

[Formula 3-3]

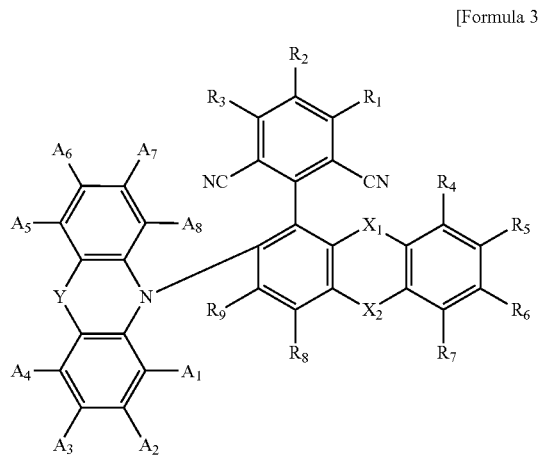

in Formula 3-1 to Formula 3-3, Y, $A_1$ to $A_8$, $X_1$, $X_2$, and $R_1$ to $R_9$ are the same as defined in Formula 1 and Formula 2.

9. The organic electroluminescence device as claimed in claim 6, wherein:

$R_1$ and $R_3$ of Formula 1 are each a hydrogen atom, and $R_2$ is a hydrogen atom, a cyano group, $SiR_{14}R_{15}$, $SR_{16}$, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

10. The organic electroluminescence device as claimed in claim 7, wherein Formula 3 is represented by any one among the following Formula 4-1 to Formula 4-3:

[Formula 4-1]
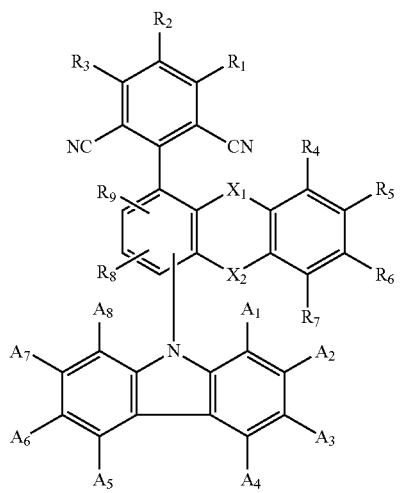
[Formula 4-2]
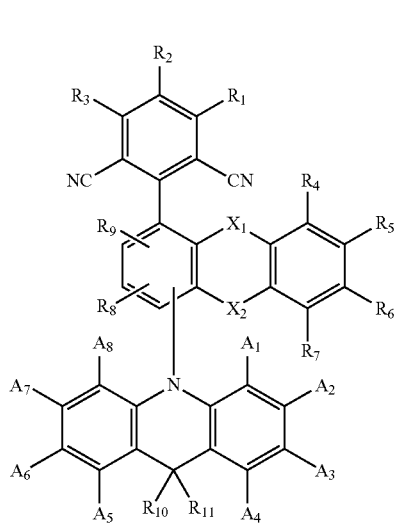
[Formula 4-3]
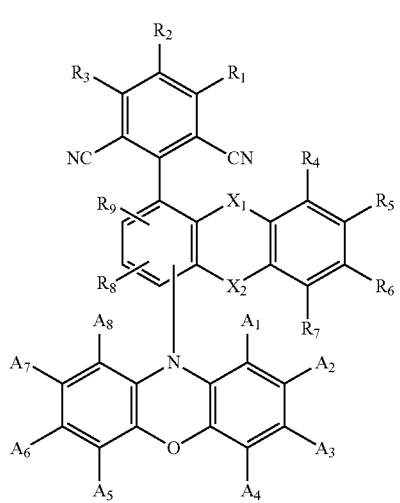
in Formula 4-1 to Formula 4-3, $A_1$ to $A_8$, $X_1$, $X_2$, and $R_1$ to $R_{11}$ are the same as defined in Formula 1 and Formula 2.
11. The organic electroluminescence device as claimed in claim 6, wherein the compound represented by Formula 1 is any one among compounds represented in following Compound Group 1:
[Compound Group 1]
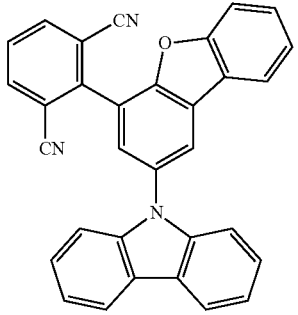
1
2
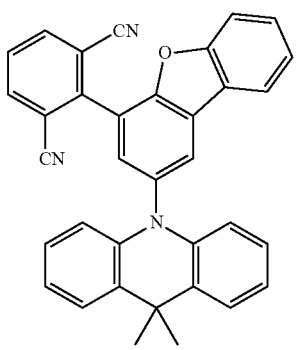
3
4

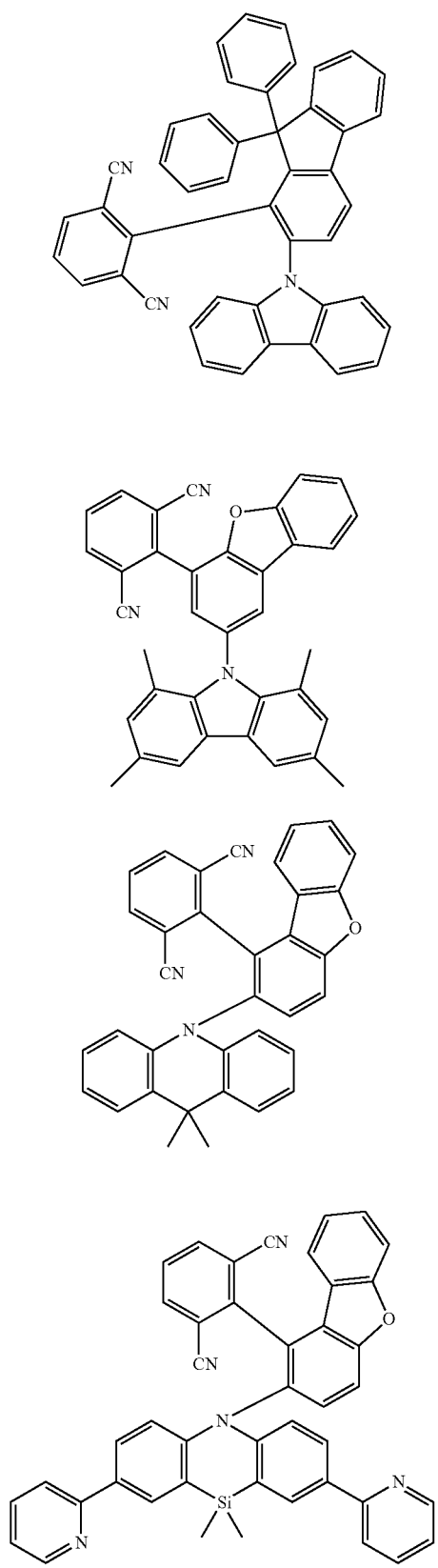
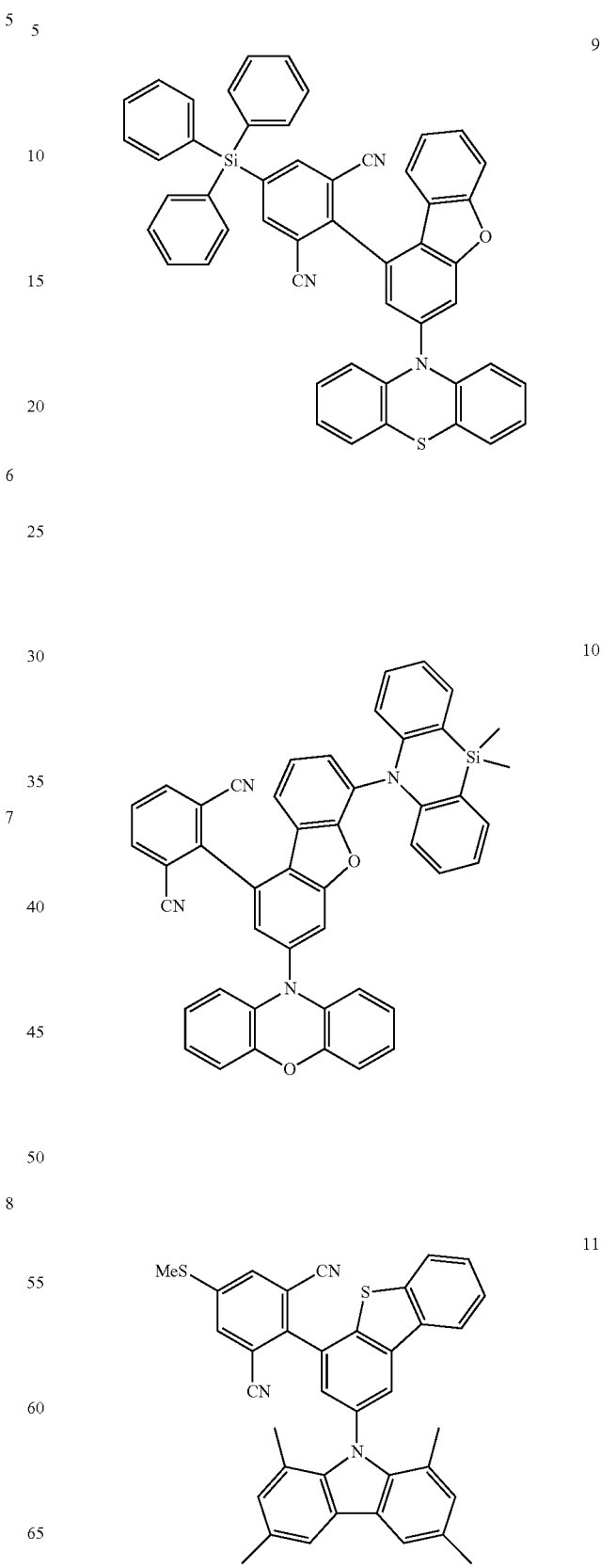

12
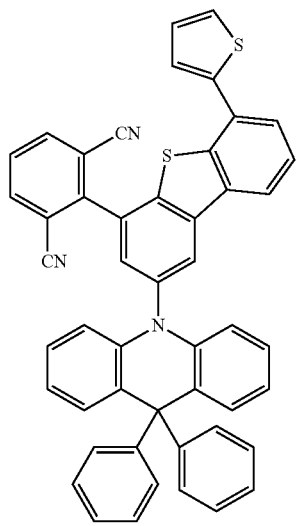
13
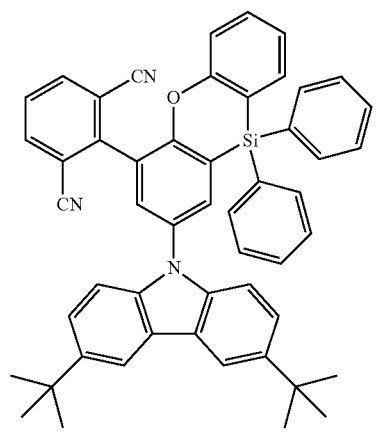
14
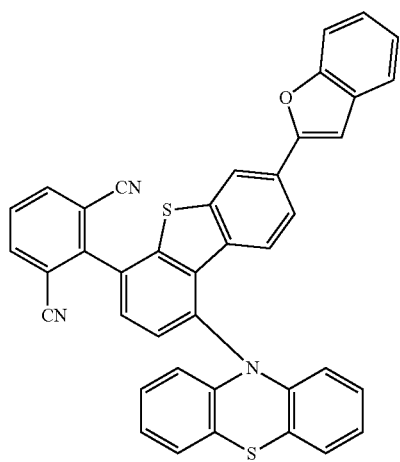
15
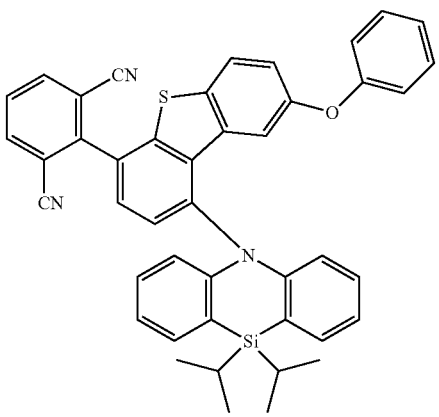
16
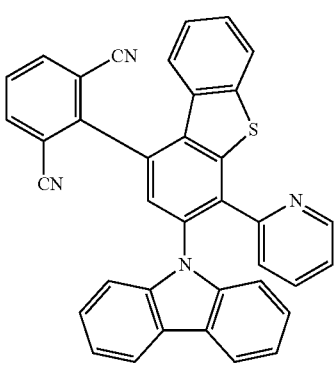
17
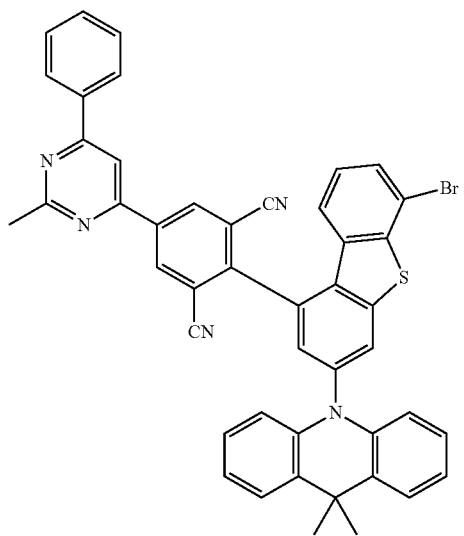

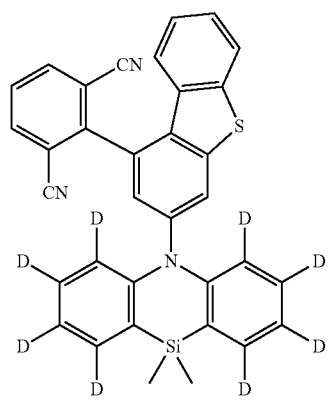
18
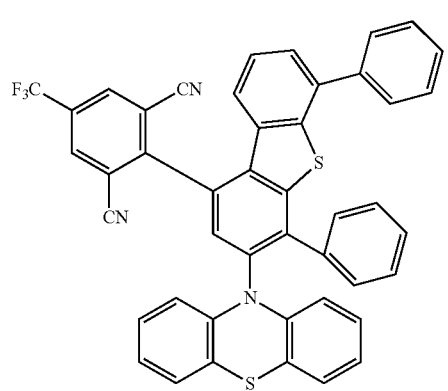
19
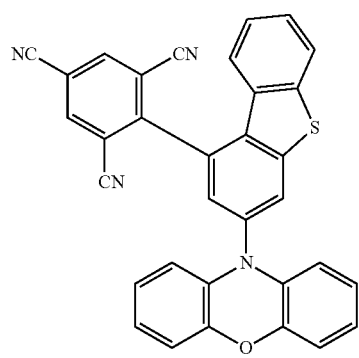
20
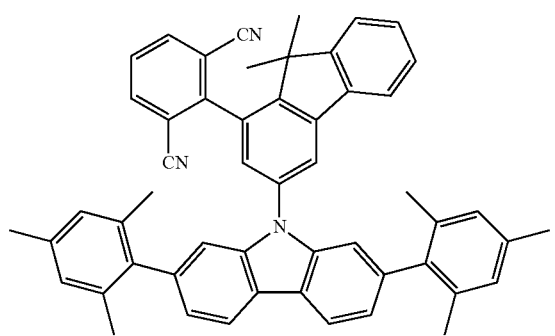
21
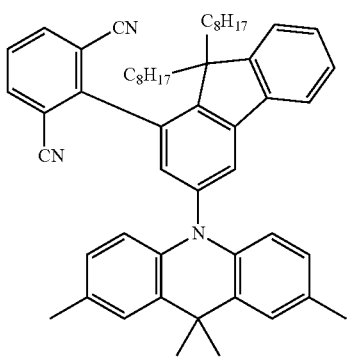
22
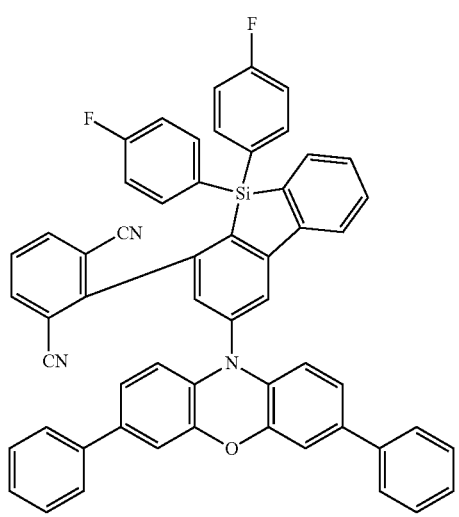
23
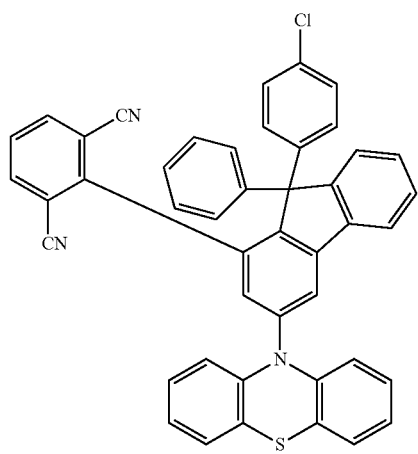
24

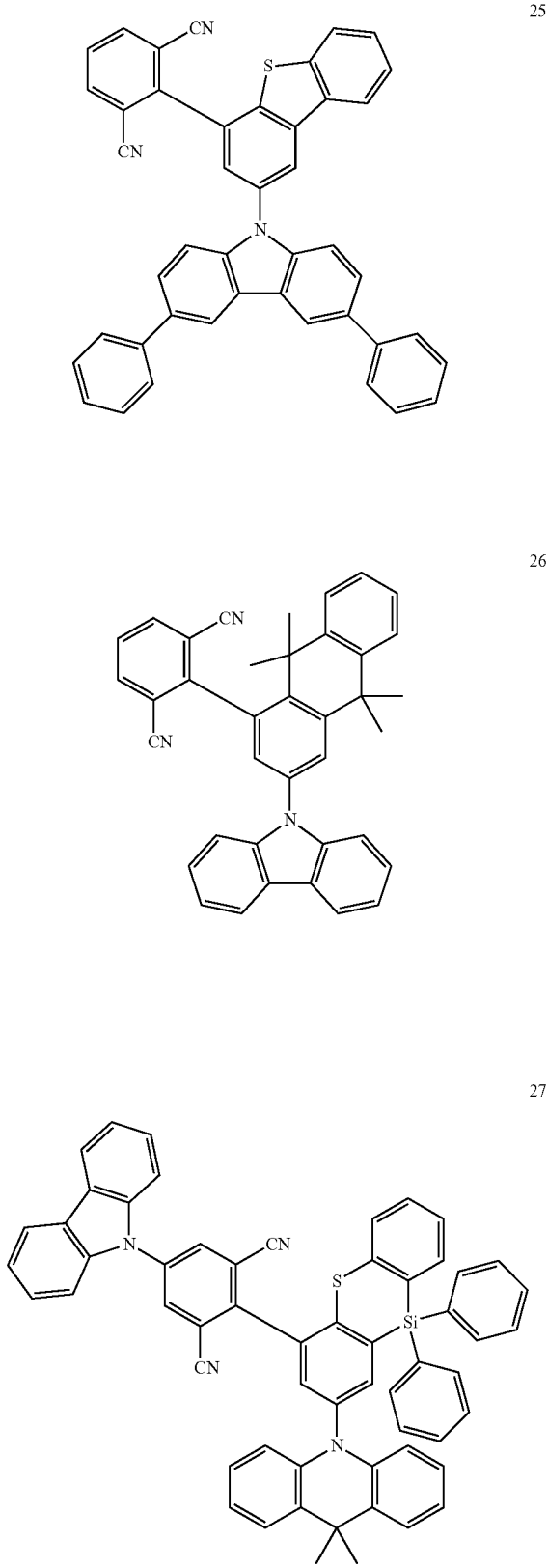
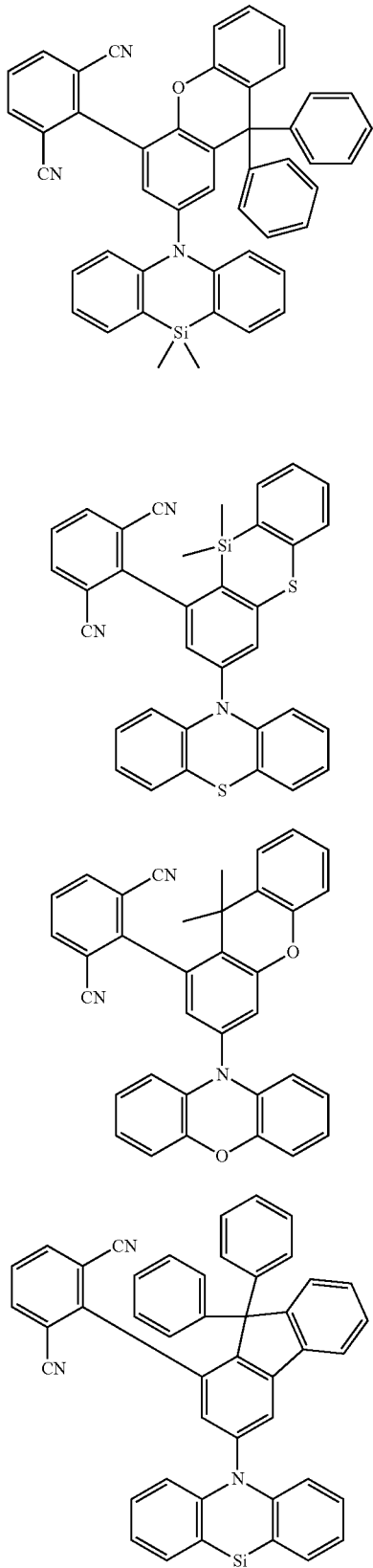

-continued

32
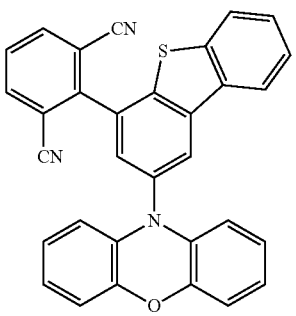

33
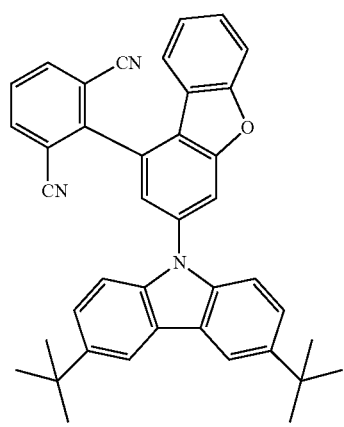

34
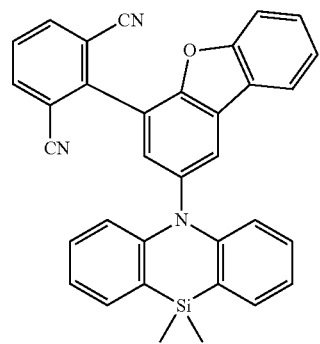

35
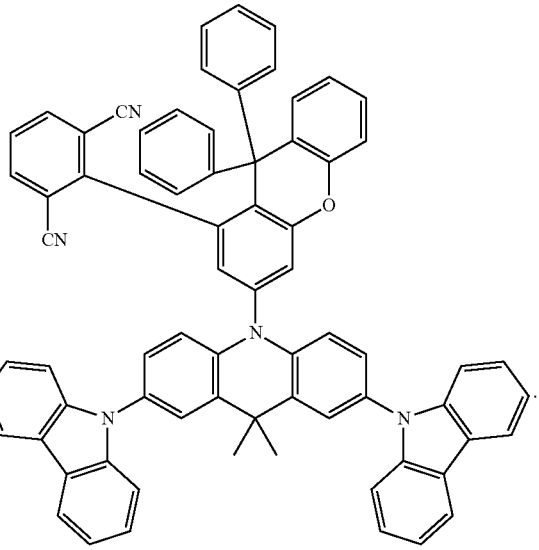

12. An organic electroluminescence device, comprising:
a first electrode;
a hole transport region on the first electrode;
an emission layer on the hole transport region;
an electron transport region on the emission layer; and
a second electrode on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and oxides thereof, and
wherein the emission layer includes a polycyclic compound represented by following Formula 1:

[Formula 1]

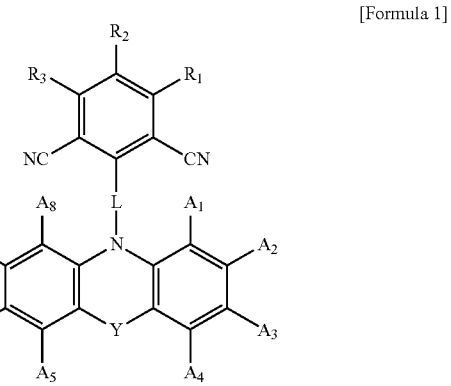

in Formula 1,
Y is $CR_{10}R_{11}$, $SiR_{12}R_{13}$, O, S, or a direct linkage,
$R_1$ to $R_3$ are each independently a hydrogen atom, a deuterium atom, a halogen atom, a cyano group, $SiR_{14}R_{15}$, $SR_{16}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms,
$A_1$ to $A_8$ and $R_{10}$ to $R_{16}$ are each independently a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and
L is represented by following Formula 2:

[Formula 2]

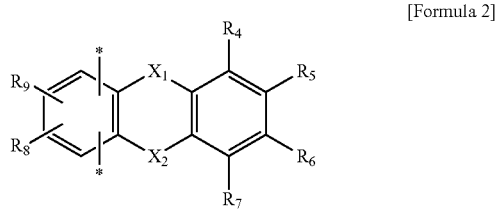

in Formula 2,
$X_1$ and $X_2$ are each independently a direct linkage, $CR_{17}R_{18}$, $SiR_{19}R_{20}$, O, or S,
$R_4$ to $R_9$ are each independently a hydrogen atom, a deuterium atom, a halogen atom, a cyano group, $SiR_{21}R_{22}$, $OR_{23}$, $SR_{24}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and $R_{17}$ to $R_{24}$ are each independently a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

13. The organic electroluminescence device as claimed in claim 12, wherein Formula 1 is represented by any one among the following Formula 3-1 to Formula 3-3:

[Formula 3-1]

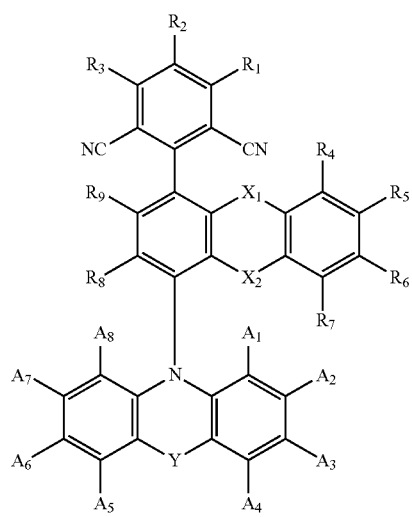

[Formula 3-2]

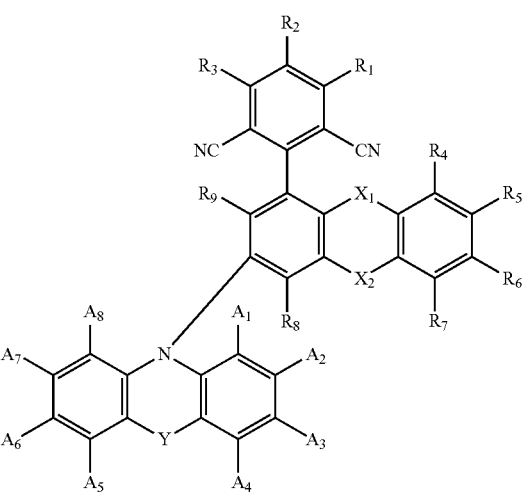

[Formula 3-3]

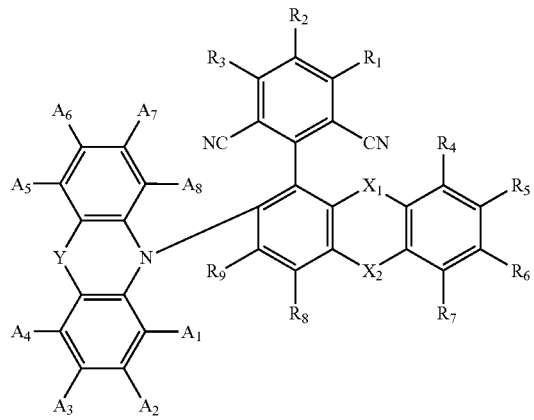

in Formula 3-1 to Formula 3-3, Y, $A_1$ to $A_8$, $X_1$, $X_2$, and $R_1$ to $R_9$ are the same as defined in Formula 1 and Formula 2.

14. A polycyclic compound represented by following Formula 1:

[Formula 1]

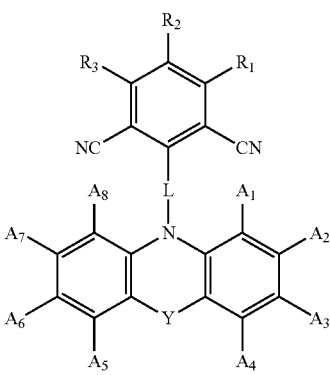

in Formula 1,

Y is $CR_{10}R_{11}$, $SiR_{12}R_{13}$, O, S, or a direct linkage, $R_1$ to $R_3$ are each independently a hydrogen atom, a deuterium atom, a halogen atom, a cyano group, $SiR_{14}R_{15}$, $SR_{16}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $A_1$ to $A_8$ and $R_{10}$ to $R_{16}$ are each independently a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and L is represented by the following Formula 2:

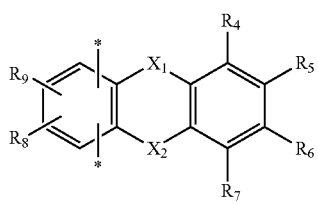

[Formula 2]

in Formula 2, $X_1$ and $X_2$ are each independently a direct linkage, $CR_{17}R_{18}$, $SiR_{19}R_{20}$, O, or S, $R_4$ to $R_9$ are each independently a hydrogen atom, a deuterium atom, a halogen atom, a cyano group, $SiR_{21}R_{22}$, $OR_{23}$, $SR_{24}$, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and $R_{17}$ to $R_{24}$ are each independently a hydrogen atom, a deuterium atom, a halogen atom, a cyano group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

15. The polycyclic compound as claimed in claim 14, wherein Formula 1 is represented by following Formula 3:

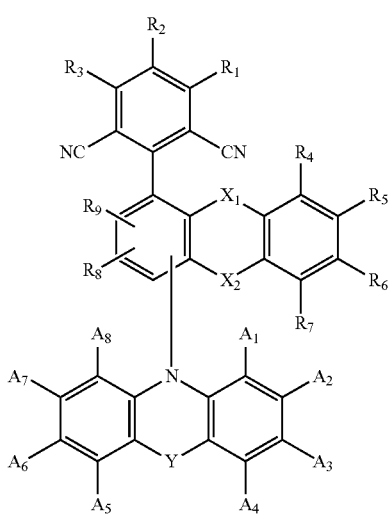

[Formula 3]

in Formula 3, Y, $A_1$ to $A_8$, $X_1$, $X_2$, and $R_1$ to $R_9$ are the same as defined in Formula 1 and Formula 2.

16. The polycyclic compound as claimed in claim 14, wherein the compound represented by Formula 1 is a material for emitting thermally activated delayed fluorescence.

17. The polycyclic compound as claimed in claim 15, wherein Formula 3 is represented by any one among the following Formula 3-1 to Formula 3-3:

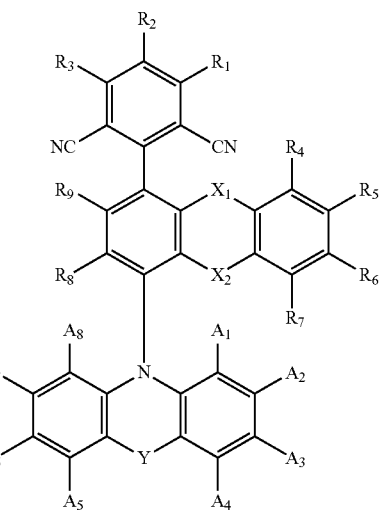

[Formula 3-1]

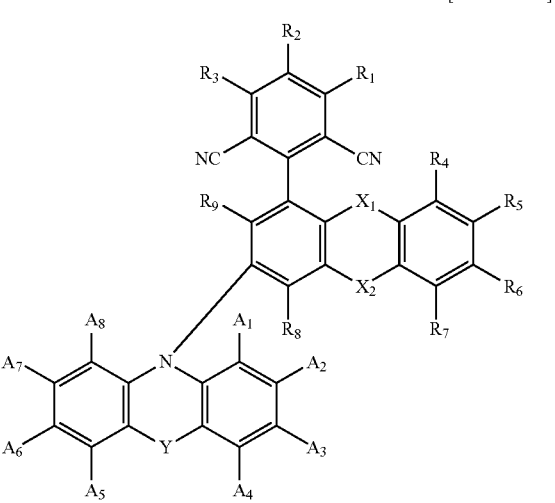

[Formula 3-2]

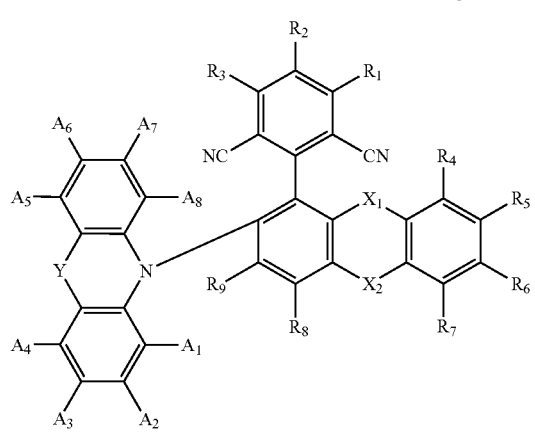

[Formula 3-3]

in Formula 3-1 to Formula 3-3, Y, $A_1$ to $A_8$, $X_1$, $X_2$, and $R_1$ to $R_9$ are the same as defined in Formula 1 and Formula 2.

18. The polycyclic compound as claimed in claim 14, wherein:

R$_1$ and R$_3$ of Formula 1 are each a hydrogen atom, and

R$_2$ is a hydrogen atom, a cyano group, SiR$_{14}$R$_{15}$, SR$_{16}$, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

19. The polycyclic compound as claimed in claim 15, wherein Formula 3 is represented by any one among the following Formula 4-1 to Formula 4-3:

[Formula 4-1]

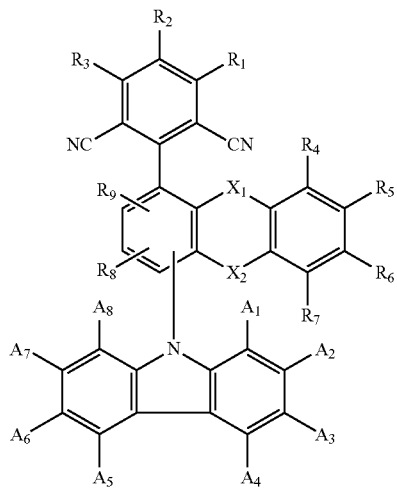

[Formula 4-2]

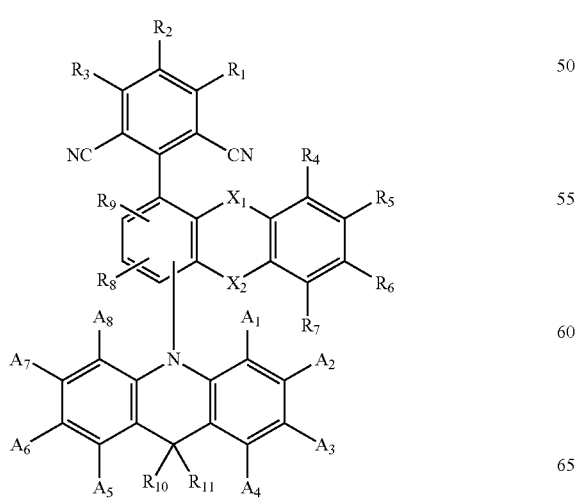

[Formula 4-3]

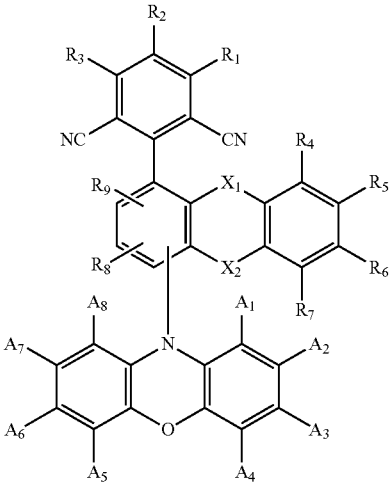

in Formula 4-1 to Formula 4-3, A$_1$ to A$_8$, X$_1$, X$_2$, and R$_1$ to R$_{11}$ are the same as defined in Formula 1 and Formula 2.

20. The polycyclic compound as claimed in claim 14, wherein the compound represented by Formula 1 is any one among compounds represented in following Compound Group 1:

[Compound Group 1]

1

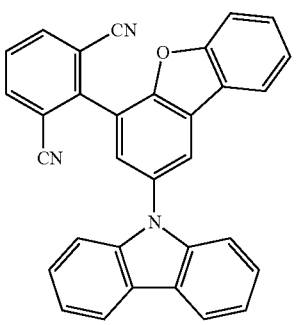

2

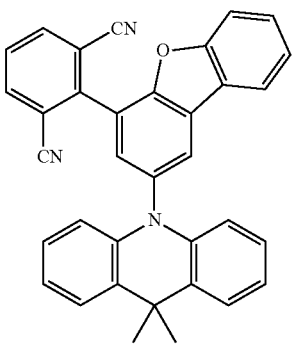

71
-continued
3
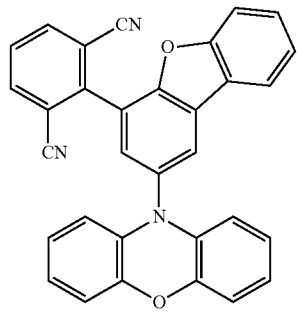
4
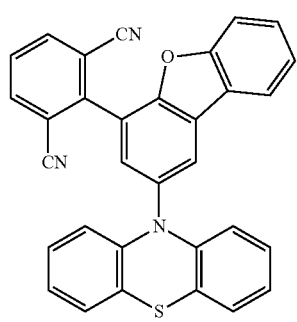
5
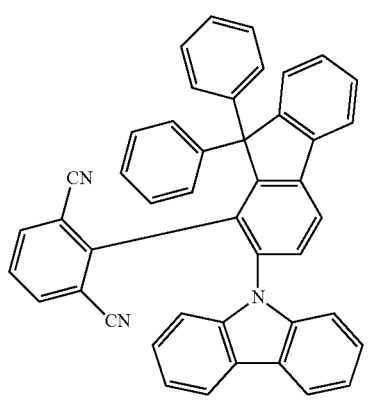
6
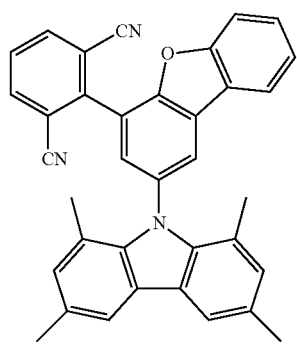
72
-continued
7
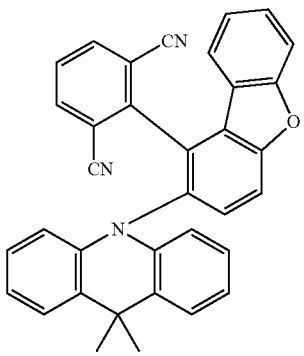
8
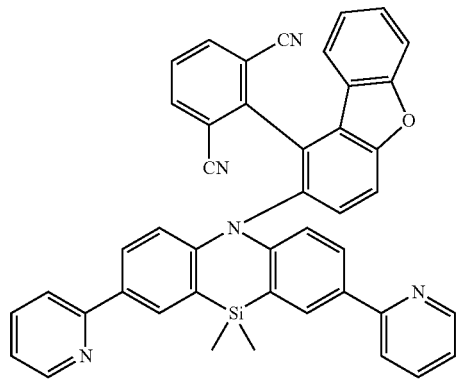
9
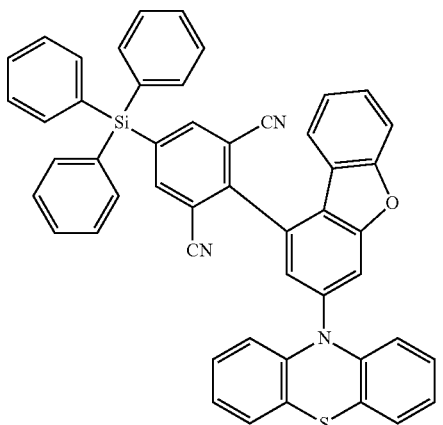
10
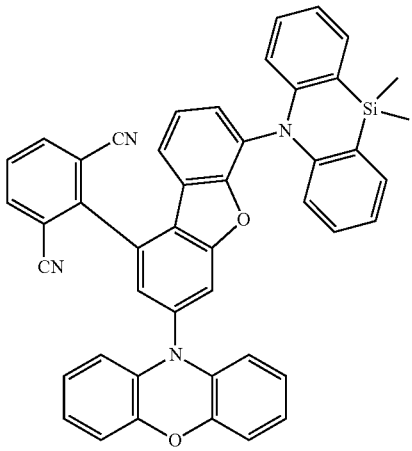

-continued
11
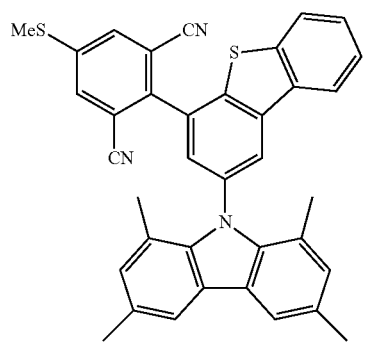
12
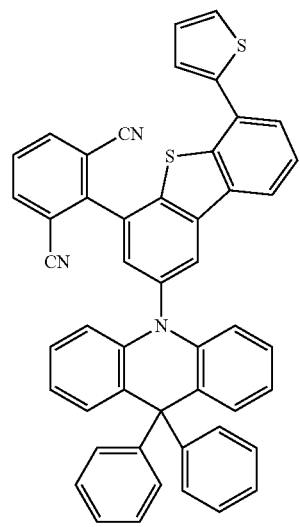
13
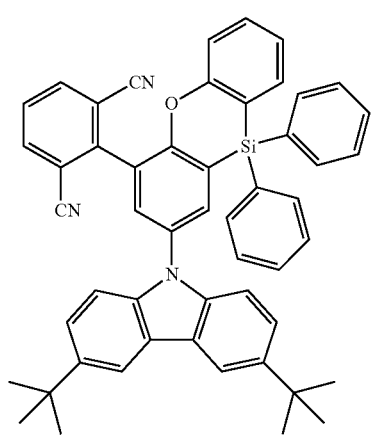
-continued
14
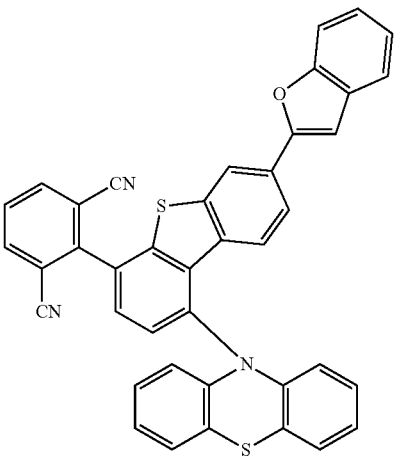
15
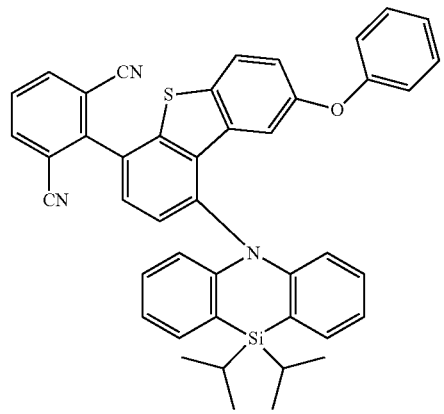
16
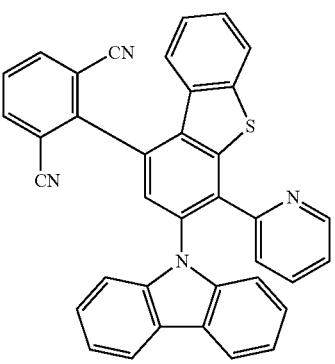

-continued
75
17
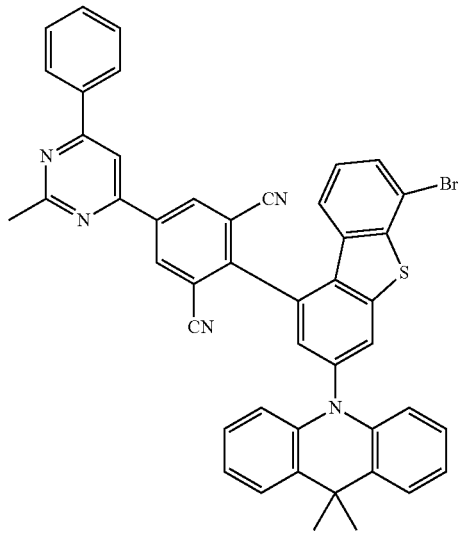
18
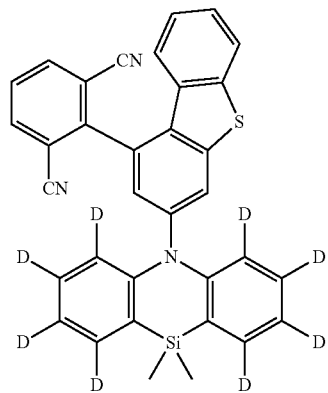
19
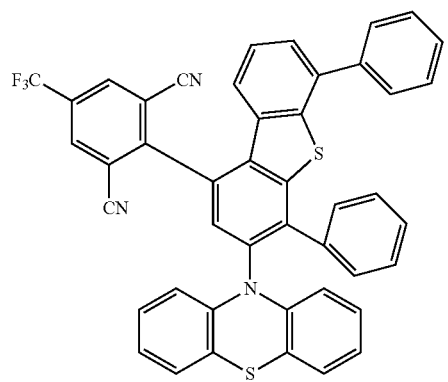
76
-continued
20
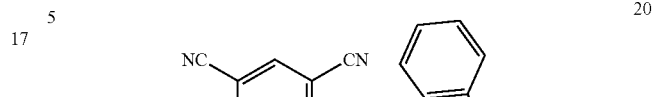
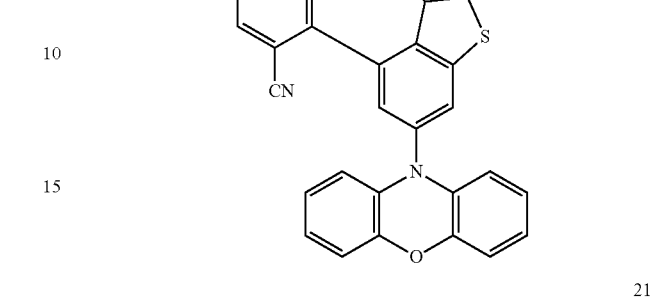
21
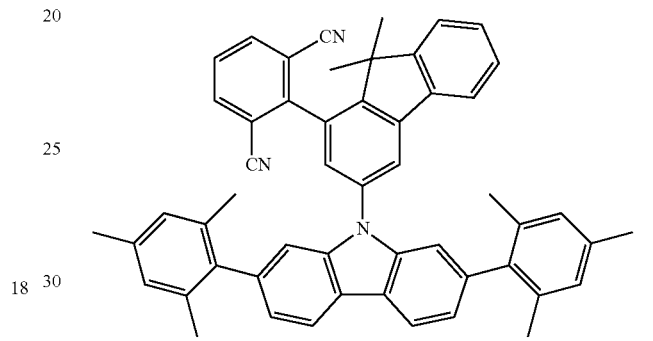
22
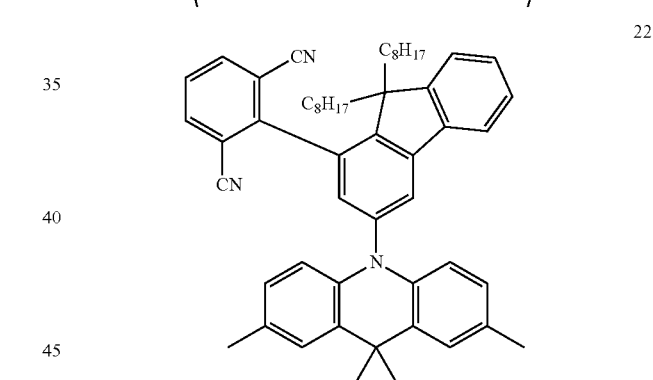
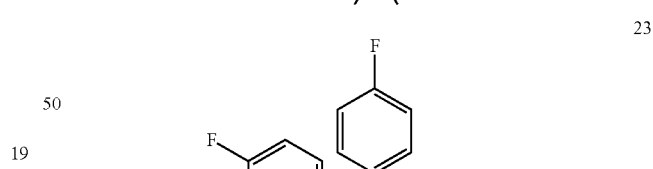
23
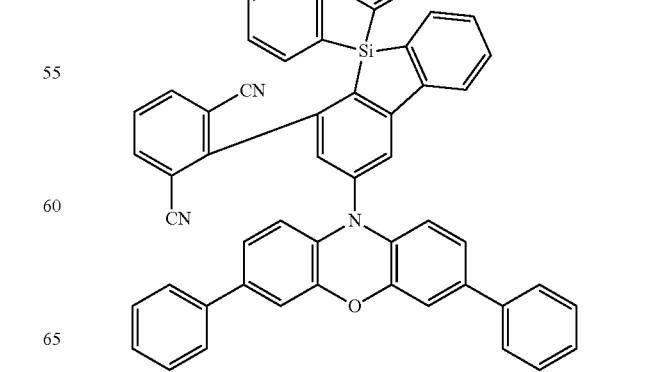

24
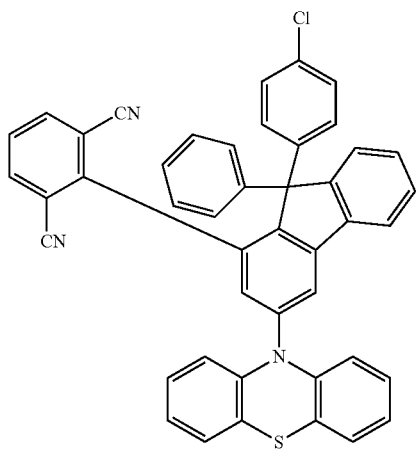
25
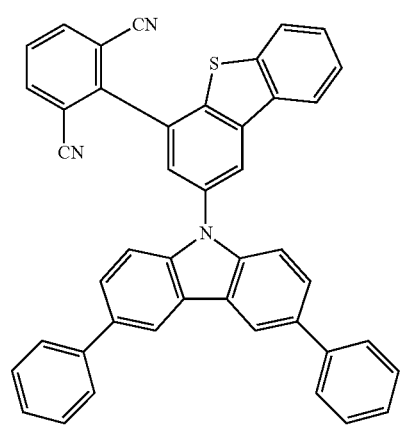
26
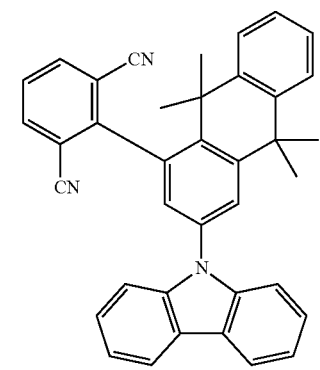
27
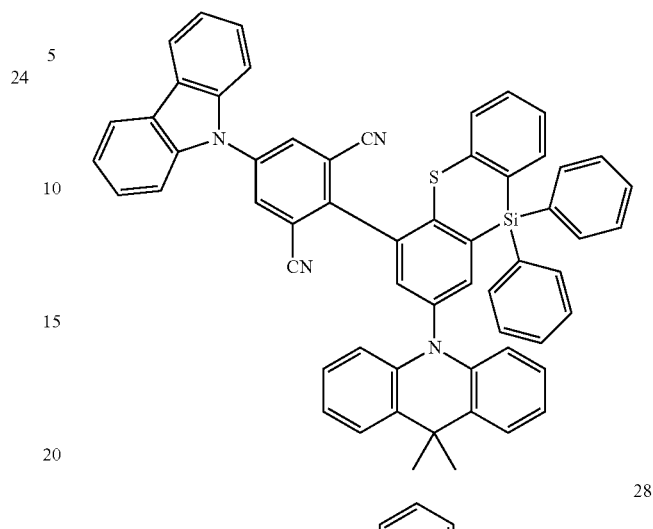
28
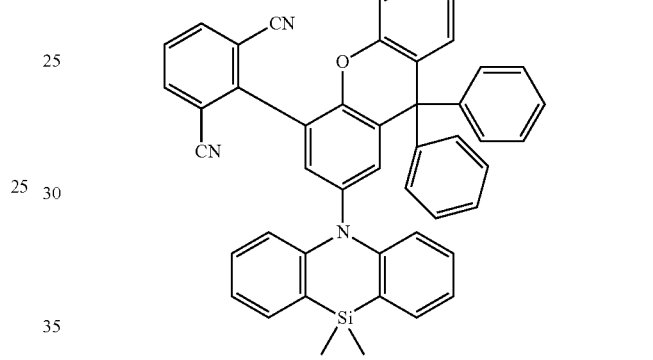
29
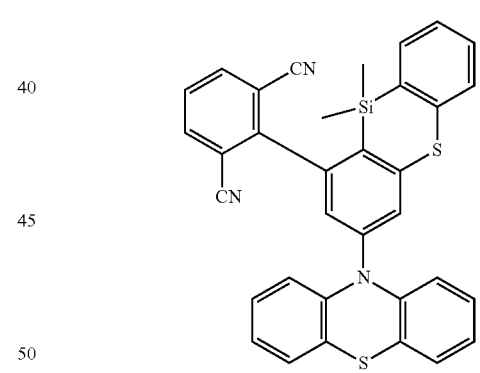
30
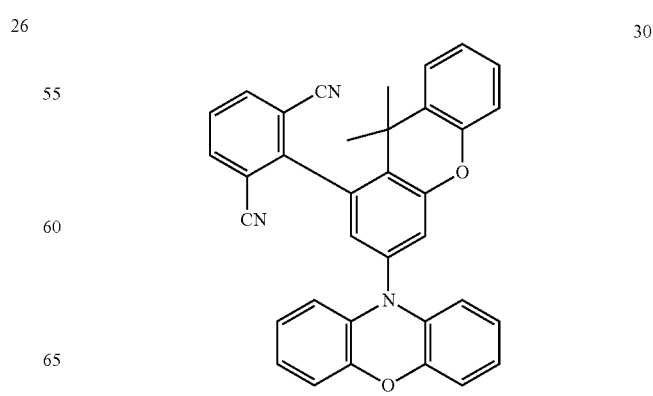

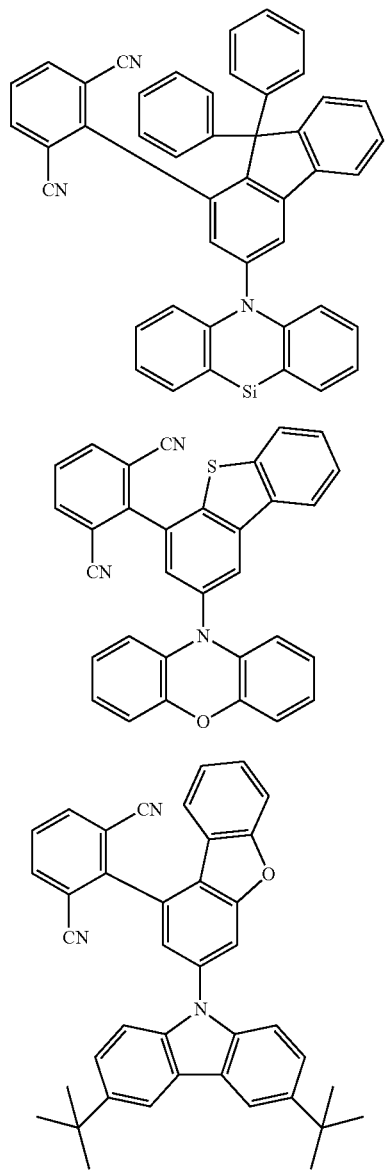
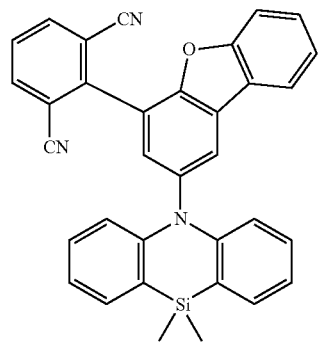
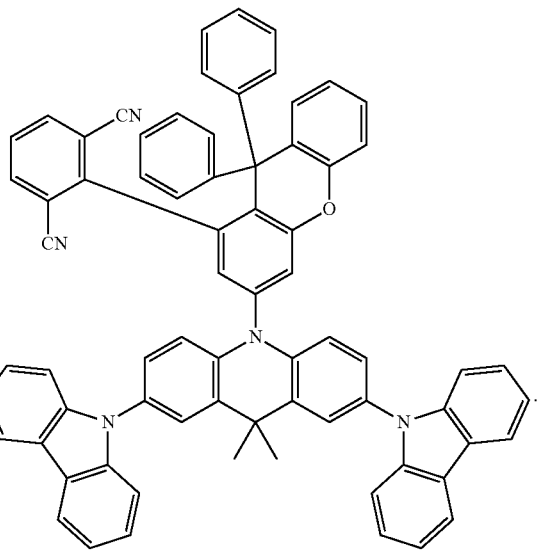
* * * * *